US008802923B2

United States Patent
Maor et al.

(10) Patent No.: US 8,802,923 B2
(45) Date of Patent: Aug. 12, 2014

(54) COMPOSITIONS AND METHODS FOR ENHANCING OIL CONTENT IN PLANTS

(75) Inventors: Rudy Maor, Rehovot (IL); Einat Sitbon, Nes Ziona (IL); Amir Avniel, New York, NY (US)

(73) Assignee: A.B. Seeds Ltd., Lod (IL)

( * ) Notice: Subject to any disclaimer, the term of this patent is extended or adjusted under 35 U.S.C. 154(b) by 335 days.

(21) Appl. No.: 12/937,026

(22) PCT Filed: Apr. 7, 2009

(86) PCT No.: PCT/IL2009/000394
§ 371 (c)(1),
(2), (4) Date: Oct. 8, 2010

(87) PCT Pub. No.: WO2009/125401
PCT Pub. Date: Oct. 15, 2009

(65) Prior Publication Data
US 2011/0030097 A1    Feb. 3, 2011

Related U.S. Application Data

(60) Provisional application No. 61/159,092, filed on Mar. 11, 2009, provisional application No. 61/043,747, filed on Apr. 10, 2008.

(51) Int. Cl.
*C12N 15/113* (2010.01)
*C12N 15/82* (2006.01)

(52) U.S. Cl.
CPC ........ *C12N 15/8247* (2013.01); *C12N 15/8218* (2013.01)
USPC ............................ 800/281; 800/285; 800/296

(58) Field of Classification Search
None
See application file for complete search history.

(56) References Cited

U.S. PATENT DOCUMENTS

| | | | | |
|---|---|---|---|---|
| 7,214,786 | B2 * | 5/2007 | Kovalic et al. | 536/23.6 |
| 7,868,149 | B2 * | 1/2011 | Boukharov et al. | 536/23.1 |
| 2004/0214272 | A1 * | 10/2004 | La Rosa et al. | 435/69.1 |
| 2004/0268441 | A1 * | 12/2004 | Vance et al. | 800/288 |
| 2005/0144669 | A1 | 6/2005 | Reinhart et al. | |
| 2006/0200878 | A1 | 9/2006 | Lutfiyya et al. | |
| 2008/0115240 | A1 | 5/2008 | Aukerman et al. | |
| 2009/0070898 | A1 | 3/2009 | Allen et al. | |

FOREIGN PATENT DOCUMENTS

| WO | WO 2006/073727 | 7/2006 |
|---|---|---|
| WO | WO 2008/133643 | 11/2008 |
| WO | WO 2010/002984 | 1/2010 |

OTHER PUBLICATIONS

Zhao et al, 2007, Genes Dev., 21:1190-1203.*
Bartel, 2004, Cell, 116:281-297.*
Liu et al, 2002, Plant Phys., 129:1732-1743.*
Dunahay et al, 1996, Applied Biochem. & Biotech., 57/58:223-231.*
Ding et al. "Differential Expression of MiRNAs in Response to Salt Stress in Maize Roots", Annals of Botany, 103(1): 29-38, Jan. 2009.
Liu et al. "Microarray-Based Analysis of Stress-Regulated MicroRNAs in *Arabidopsis thaliana*", RNA, 14: 1-8, 2008.
Pant et al. "Identification of Nutrient-Responsive *Arabidopsis* and Rapeseed MicroRNAs by Comprehensive Real-Time Polymerase Chain Reaction Profiling and Small RNA Sequencing 1[C][W][OA]", Plant Physiology, 150: 1541-1555, Jul. 2009.
Office Action Dated Sep. 20, 2013 From the Israel Patent Office Re. Application No. 208003 and Its Translation Into English.

\* cited by examiner

*Primary Examiner* — Ashwin Mehta
*Assistant Examiner* — Jason Deveau Rosen

(57) ABSTRACT

The present invention provides transgenic plants with altered oil content. The invention further provides nucleic acid sequences and methods for generating such plants.

10 Claims, 10 Drawing Sheets

SEQUENCE LISTING

```
<160> NUMBER OF SEQ ID NOS: 88

<210> SEQ ID NO 1
<211> LENGTH: 21
<212> TYPE: RNA
<213> ORGANISM: Chlamydomonas reinhardtii

<400> SEQUENCE: 1
aaggugccau auccagggac c                                                 21

<210> SEQ ID NO 2
<211> LENGTH: 22
<212> TYPE: RNA
<213> ORGANISM: Chlamydomonas reinhardtii

<400> SEQUENCE: 2
ugagaagaug cgguccguug gc                                                22
```

```
<210> SEQ ID NO 3
<211> LENGTH: 22
<212> TYPE: RNA
<213> ORGANISM: Chlamydomonas reinhardtii

<400> SEQUENCE: 3
ugacgcguuu gauagcagga uc                                              22

<210> SEQ ID NO 4
<211> LENGTH: 19
<212> TYPE: RNA
<213> ORGANISM: Chlamydomonas reinhardtii

<400> SEQUENCE: 4
acuacgucaa uaaggcagc                                                  19

<210> SEQ ID NO 5
<211> LENGTH: 21
<212> TYPE: RNA
<213> ORGANISM: Chlamydomonas reinhardtii

<400> SEQUENCE: 5
agcagcgucg ggcucgaccg c                                               21

<210> SEQ ID NO 6
<211> LENGTH: 21
<212> TYPE: RNA
<213> ORGANISM: Chlamydomonas reinhardtii

<400> SEQUENCE: 6
ccaaggucau cgguucgauc c                                               21

<210> SEQ ID NO 7
<211> LENGTH: 21
<212> TYPE: RNA
<213> ORGANISM: Chlamydomonas reinhardtii

<400> SEQUENCE: 7
aaucgagaug cugaccgaga u                                               21

<210> SEQ ID NO 8
<211> LENGTH: 21
<212> TYPE: RNA
<213> ORGANISM: Chlamydomonas reinhardtii

<400> SEQUENCE: 8
ucucaggagg acaucgccac u                                               21

<210> SEQ ID NO 9
<211> LENGTH: 21
<212> TYPE: RNA
<213> ORGANISM: Chlamydomonas reinhardtii

<400> SEQUENCE: 9
uuggggccca gcagguccug g                                               21

<210> SEQ ID NO 10
<211> LENGTH: 21
<212> TYPE: RNA
<213> ORGANISM: Chlamydomonas reinhardtii

<400> SEQUENCE: 10
```

-continued uggcguugac ccugucggug g                                          21

<210> SEQ ID NO 11
<211> LENGTH: 22
<212> TYPE: RNA
<213> ORGANISM: Chlamydomonas reinhardtii

<400> SEQUENCE: 11
ucggacaaca ccgaccccca gc                                         22

<210> SEQ ID NO 12
<211> LENGTH: 21
<212> TYPE: RNA
<213> ORGANISM: Chlamydomonas reinhardtii

<400> SEQUENCE: 12
uguugucuga cauggagggu c                                          21

<210> SEQ ID NO 13
<211> LENGTH: 21
<212> TYPE: RNA
<213> ORGANISM: Chlamydomonas reinhardtii

<400> SEQUENCE: 13
uccggggcuc auaaccuguu g                                          21

<210> SEQ ID NO 14
<211> LENGTH: 21
<212> TYPE: RNA
<213> ORGANISM: Chlamydomonas reinhardtii

<400> SEQUENCE: 14
uccggggcuc auaaccuguu a                                          21

<210> SEQ ID NO 15
<211> LENGTH: 21
<212> TYPE: RNA
<213> ORGANISM: Chlamydomonas reinhardtii

<400> SEQUENCE: 15
uaagaaggug cgcugucuug a                                          21

<210> SEQ ID NO 16
<211> LENGTH: 22
<212> TYPE: RNA
<213> ORGANISM: Chlamydomonas reinhardtii

<400> SEQUENCE: 16
uaguccugca cgaggaagga gc                                         22

<210> SEQ ID NO 17
<211> LENGTH: 21
<212> TYPE: RNA
<213> ORGANISM: Chlamydomonas reinhardtii

<400> SEQUENCE: 17
uucagguagc gggaccaggu g                                          21

<210> SEQ ID NO 18
<211> LENGTH: 20
<212> TYPE: RNA
<213> ORGANISM: Chlamydomonas reinhardtii

<400> SEQUENCE: 18

| | |
|---|---|
| uugcccuuuu uaagcagggc | 20 |

<210> SEQ ID NO 19
<211> LENGTH: 21
<212> TYPE: RNA
<213> ORGANISM: Chlamydomonas reinhardtii

<400> SEQUENCE: 19

| | |
|---|---|
| ugacaaggaa gcagagcgga u | 21 |

<210> SEQ ID NO 20
<211> LENGTH: 19
<212> TYPE: RNA
<213> ORGANISM: Chlamydomonas reinhardtii

<400> SEQUENCE: 20

| | |
|---|---|
| ggacccgugc gggaaggga | 19 |

<210> SEQ ID NO 21
<211> LENGTH: 19
<212> TYPE: RNA
<213> ORGANISM: Chlamydomonas reinhardtii

<400> SEQUENCE: 21

| | |
|---|---|
| ggguguqaug auuugaaac | 19 |

<210> SEQ ID NO 22
<211> LENGTH: 21
<212> TYPE: RNA
<213> ORGANISM: Chlamydomonas reinhardtii

<400> SEQUENCE: 22

| | |
|---|---|
| uuggacaag gccaaguccg a | 21 |

<210> SEQ ID NO 23
<211> LENGTH: 17
<212> TYPE: RNA
<213> ORGANISM: Chlamydomonas reinhardtii

<400> SEQUENCE: 23

| | |
|---|---|
| agcacggaag gcgaaga | 17 |

<210> SEQ ID NO 24
<211> LENGTH: 21
<212> TYPE: RNA
<213> ORGANISM: Chlamydomonas reinhardtii

<400> SEQUENCE: 24

| | |
|---|---|
| uguggauguu gcuugcugga u | 21 |

<210> SEQ ID NO 25
<211> LENGTH: 23
<212> TYPE: RNA
<213> ORGANISM: Chlamydomonas reinhardtii

<400> SEQUENCE: 25

| | |
|---|---|
| uggaguggag uggaguggag ugg | 23 |

<210> SEQ ID NO 26
<211> LENGTH: 21
<212> TYPE: RNA
<213> ORGANISM: Chlamydomonas reinhardtii

```
<400> SEQUENCE: 26
uccaggaucu agcugucguc u                                          21

<210> SEQ ID NO 27
<211> LENGTH: 21
<212> TYPE: RNA
<213> ORGANISM: Chlamydomonas reinhardtii

<400> SEQUENCE: 27
uuguggaugg ggcccauccu g                                          21

<210> SEQ ID NO 28
<211> LENGTH: 19
<212> TYPE: RNA
<213> ORGANISM: Chlamydomonas reinhardtii

<400> SEQUENCE: 28
auggggccca uccugauug                                             19

<210> SEQ ID NO 29
<211> LENGTH: 21
<212> TYPE: RNA
<213> ORGANISM: Chlamydomonas reinhardtii

<400> SEQUENCE: 29
uacauucuug gagacacggc c                                          21

<210> SEQ ID NO 30
<211> LENGTH: 21
<212> TYPE: RNA
<213> ORGANISM: Chlamydomonas reinhardtii

<400> SEQUENCE: 30 aggggggaagc uuuaucggaa u                                         21

<210> SEQ ID NO 31
<211> LENGTH: 20
<212> TYPE: RNA
<213> ORGANISM: Chlamydomonas reinhardtii

<400> SEQUENCE: 31
uacugcaggg gcaucucgau                                            20

<210> SEQ ID NO 32
<211> LENGTH: 21
<212> TYPE: RNA
<213> ORGANISM: Chlamydomonas reinhardtii

<400> SEQUENCE: 32
ccugugagcg caaucagcgg u                                          21

<210> SEQ ID NO 33
<211> LENGTH: 21
<212> TYPE: RNA
<213> ORGANISM: Chlamydomonas reinhardtii

<400> SEQUENCE: 33
ucauguguac caaggacgug a                                          21

<210> SEQ ID NO 34
<211> LENGTH: 21
<212> TYPE: RNA
<213> ORGANISM: Chlamydomonas reinhardtii
```

```
<400> SEQUENCE: 34
acauccuugg uacacaugaa a                                              21

<210> SEQ ID NO 35
<211> LENGTH: 19
<212> TYPE: RNA
<213> ORGANISM: Chlamydomonas reinhardtii

<400> SEQUENCE: 35
cgaccccgcg aucggaagu                                                 19

<210> SEQ ID NO 36
<211> LENGTH: 22
<212> TYPE: RNA
<213> ORGANISM: Chlamydomonas reinhardtii

<400> SEQUENCE: 36
uccgaaaagc ccuauguuug cu                                             22

<210> SEQ ID NO 37
<211> LENGTH: 21
<212> TYPE: RNA
<213> ORGANISM: Chlamydomonas reinhardtii

<400> SEQUENCE: 37
aacgagggga ugacgagcac g                                              21

<210> SEQ ID NO 38
<211> LENGTH: 22
<212> TYPE: RNA
<213> ORGANISM: Chlamydomonas reinhardtii

<400> SEQUENCE: 38
ugcagcugcg ggcccgagca cu                                             22

<210> SEQ ID NO 39
<211> LENGTH: 19
<212> TYPE: RNA
<213> ORGANISM: Chlamydomonas reinhardtii

<400> SEQUENCE: 39
uuggggcccg agaugcggc                                                 19

<210> SEQ ID NO 40
<211> LENGTH: 293
<212> TYPE: RNA
<213> ORGANISM: Chlamydomonas reinhardtii

<400> SEQUENCE: 40
ugccgggcug gggccgggcg ggcugugauc gaccuggagg ucccuggaua uggccacuuc     60
gagguugugg ucacacacuc aguccgggga ccucggccca guugcugguu cuaugcucug    120
acuacccgac aagcaagcuu ggggccgccc cccacauugg uccugcggua gucagaacag    180
agcacuagcg acugggccga gguaacccgc acugagugcg ugaccacaac cucgaaggug    240
ccauauccag ggaccuccag gucgaucaca gcccgcccgg ccccagcgcg gca           293

<210> SEQ ID NO 41
<211> LENGTH: 230
<212> TYPE: RNA
<213> ORGANISM: Chlamydomonas reinhardtii
```

```
<400> SEQUENCE: 41
guggguuuug agaagaugcg guccguuggc uauaauguug acagaccacc cgcucccuua      60
cugacgcagu ugacgcguuu gauagcagga ucauaguacg ggaccaguuc cccuaccaac     120
uggucccgua accacauga uccugcuauc aaaggcguca acuacgucaa uaaggcagcg     180 ggugucaau auacauuauu gccaacggac cgguucuccu caaaugucac              230

<210> SEQ ID NO 42
<211> LENGTH: 227
<212> TYPE: RNA
<213> ORGANISM: Chlamydomonas reinhardtii

<400> SEQUENCE: 42
ccgcugcagc cggucaggug caccggagg ugccggagcg guuggggung cggggcccgc      60
agguagcugc cguugagccc gacgcugcug ccgccgcgcc ggugcugcug cgcggcagca     120
ccugaccggc ugcagcagcg ucgggcucga ccgcagccac cugcgggucc gcagcccca     180 gcagcuaccg acugcaccug accggcugca ccugaccggc ugcaggg                227

<210> SEQ ID NO 43
<211> LENGTH: 256
<212> TYPE: RNA
<213> ORGANISM: Chlamydomonas reinhardtii

<400> SEQUENCE: 43
acggaaacgg uuguacgggg cgccguacgg ugguugugg agaggggggg gcuggguggau      60 augacguggg ccuguuagcu caguugguua gagcguggug cuaauaacgc caaggucauc     120
gguucgaucc cgauacgggc cagcggaagc cuuuugggcc acgcgccac gcugcaauac     180 gcgcacgaga ggccuuaagg auguaaggcc uauaugccug ucggacggg cggucagacg     240 acauuugggg guucgg                                                 256

<210> SEQ ID NO 44
<211> LENGTH: 256
<212> TYPE: RNA
<213> ORGANISM: Chlamydomonas reinhardtii

<400> SEQUENCE: 44
aaugcgggac gucugcgccg cacaugucuc aggaggacau cgccacuauu agcaagcuac      60
uucaggguau cucggucagc auuucguuug gcaagaugue cgcuucaggu acacgccgcu     120
cacgcgauga aggcgucauc gcaugagcgg cgcguacccg gaguggacgu cuugccaauc     180
gagaugcuga ccgagauacc cuccagcagc uugcuacuac ggacgaucuc uuccugagac     240
augugcgggg cagacg                                                 256

<210> SEQ ID NO 45
<211> LENGTH: 256
<212> TYPE: RNA
<213> ORGANISM: Chlamydomonas reinhardtii

<400> SEQUENCE: 45
cccaacgugg aagggcauga ccuccucccu ucugcagacc uaggucagaa ggaccaggac      60
cugcugggcc ccaaggucau ggucgcaaug cuggucaacg ccaccgagag ggucaacacc     120
acccagcagc ucugggcgga caucaagcag aagacguccu ccagcgggag gccgucuucu     180
gcuugauguc cgcccacagc ugcugauugg cguugacccu gucgguggcc uugaccagca     240
ucgcggcaau gaccuu                                                 256
```

```
<210> SEQ ID NO 46
<211> LENGTH: 114
<212> TYPE: RNA
<213> ORGANISM: Chlamydomonas reinhardtii

<400> SEQUENCE: 46
cgaccgccuc gggcccgcua ugucggacaa caccgacccc cagcccgcca acaaggagau      60
ggcguuggcg ggcuggdgguc ggucguuguguucu gacauggagg gucccaggca gucg       114
```

```
<210> SEQ ID NO 46
<211> LENGTH: 114
<212> TYPE: RNA
<213> ORGANISM: Chlamydomonas reinhardtii

<400> SEQUENCE: 46
cgaccgccuc gggcccgcua ugucggacaa caccgacccc cagcccgcca acaaggagau      60
ggcguuggcg ggcuggdguc gguguugucu gacauggagg gucccaggca gucg            114

<210> SEQ ID NO 47
<211> LENGTH: 110
<212> TYPE: RNA
<213> ORGANISM: Chlamydomonas reinhardtii

<400> SEQUENCE: 47
ccggccgcgg caguccgggg cucauaaccu guugacgcgc gcagcccgcg ggcagucccu      60
gcgggccgcg cggcgcuaac ggggguguggg acccggacug acgcggccgg                110

<210> SEQ ID NO 48
<211> LENGTH: 144
<212> TYPE: RNA
<213> ORGANISM: Chlamydomonas reinhardtii

<400> SEQUENCE: 48
guggugugug ccgcucaccg gccacggcag uccggggcuc auaaccuguu aacgcgcgca      60
gcccgcaggc aguccc ugcg ggccgcgcgg ugcuaacggg uugugggacc cggacugacg    120
cggcuggcau gugacaggcc ccac                                             144

<210> SEQ ID NO 49
<211> LENGTH: 130
<212> TYPE: RNA
<213> ORGANISM: Chlamydomonas reinhardtii

<400> SEQUENCE: 49 gggggudauuc acggcaccgu caagacggcg caccuucuua acguccuucg gugcuugcuu      60
gcacacacuc aagcaggcac cgaagggcgu uaagaaggug cgcugucuug acggugccgu     120
gaauaccuuc                                                             130

<210> SEQ ID NO 50
<211> LENGTH: 100
<212> TYPE: RNA
<213> ORGANISM: Chlamydomonas reinhardtii

<400> SEQUENCE: 50
ugaggcucgu uccucaagca ggacucaaag aacccgauca gcuugucgag cacgacaagg      60
ugaucguguu uucuuagucc ugcacgagga aggagcccca                            100

<210> SEQ ID NO 51
<211> LENGTH: 137
<212> TYPE: RNA
<213> ORGANISM: Chlamydomonas reinhardtii

<400> SEQUENCE: 51
uccugggcgc aguguuccag cugcaguaca ccugguccccg cuauuugaau cucgcugauc      60
ggcaccaugg gguggugguu gaucagcgcu auucagguag cgggaccagg uguacugcag     120
ccggaacacu gccagga                                                     137
```

<210> SEQ ID NO 52
<211> LENGTH: 256
<212> TYPE: RNA
<213> ORGANISM: Chlamydomonas reinhardtii

<400> SEQUENCE: 52
uuugcaugcu cucgcccgcu acacaaacac gaaugcucaa acgcucccuu cccgcacggg    60
uccuuccggc ugcgccgguc aagccugccc ugcuuaaaaa gggcaaaguu cgggcugaca   120
aggaagcaga gcggauccuc cagagccuca cagaccucaa gaaggucggg uucacaagca   180
aaugacgccu gcuuaaccag gucguugccg ccggaaaagu cgucagcagc guggcagccu   240
gcuuagcagg cgucau                                                   256

<210> SEQ ID NO 53
<211> LENGTH: 89
<212> TYPE: RNA
<213> ORGANISM: Chlamydomonas reinhardtii

<400> SEQUENCE: 53
gagcaucaug caucguuaca cccccaccg ugcaccuuca cgcucaugcg cagcacugug     60
caugcuuggg gugugaugau uugaaacuu                                      89

<210> SEQ ID NO 54
<211> LENGTH: 193
<212> TYPE: RNA
<213> ORGANISM: Chlamydomonas reinhardtii

<400> SEQUENCE: 54
gcggcuuggu cuuccgcgg uggccuccuc cucaaucuug gccuugcgcg cuucgggcuu     60
ggccuggucu acacagcagg cagggguuggg aagcucccuu acccgccug cugugugggac  120 aaggccaagu ccgaagcacg gaaggcgaag auugaggagg agcgugcagu gcgggucau    180 gggucgugcc ugc                                                      193

<210> SEQ ID NO 55
<211> LENGTH: 96
<212> TYPE: RNA
<213> ORGANISM: Chlamydomonas reinhardtii

<400> SEQUENCE: 55
uacgguaucc agcaagcaac auccacauaa gccggggguug uagcaacac aucuaccaac    60 cccggcuuau guggauguug cuugcuggau accgug                              96

<210> SEQ ID NO 56
<211> LENGTH: 187
<212> TYPE: RNA
<213> ORGANISM: Chlamydomonas reinhardtii

<400> SEQUENCE: 56
gggaguggag uggaguggag uggaguggag uggaguggga gugggagugg gugcaagggc    60
gugggugggu gggugcggcg ggcgcgcuug ucgugacacc uugacucauc accccgccuc   120
caacgccucc aacgccucgc uacucccccu gcaaccccu ucccacgcc ccgucccuc     180 cgcuccc                                                             187

<210> SEQ ID NO 57
<211> LENGTH: 290
<212> TYPE: RNA
<213> ORGANISM: Chlamydomonas reinhardtii

<400> SEQUENCE: 57

```
gcucacgaca agggugccau cgucaccggu cuaaucuaau gccaggcaac cagggaagac        60
acaggaucca uuuucuagug ccuggcuggg aucaaugcaa gaugauaguu ggauccugga       120
cgccgaaggc caucaugcgg ugucaaccgc augacggccg uuggcgucca ggaucuagcu       180
gucgucuugg auugauccca gccaggcgcu uggagaugga cccacggucu ucccucccuu       240
guugccuggu uccgagcag accggcgacg auggcaccac cgucguuggc                   290
```

<210> SEQ ID NO 58
<211> LENGTH: 706
<212> TYPE: RNA
<213> ORGANISM: Chlamydomonas reinhardtii

<400> SEQUENCE: 58

```
gugccgcugc ucgugcugcu acuggauggg acuucggugg gccacagcgu gcggcuggcc        60
gcuacggugc ugagcuucac caacagcgcg uaccgcaugg cucugggucu gggccuggac       120
uucuggacug cccccacacg gcgccagcuc gcgcacugcu caacagcgcu gauaacuuuc       180
aaggugcucg cgacugugcu ugggauggg gcccauccug auugugggg uggugucaug       240
gcugcggggc gcacuguuug ccaucugggc agcagcccua uagcuaugcu caagcacauu       300
ggccagaaua gugucaagau guugcugacu uagcagagga uagcuccccc ggccacaacc       360
ccgcuauccu cugcuaaguc agcaacgucu ugacacugau cuggccaaug ugcuugagca       420
uagcuauagg gcugcugccc agauggcaaa cagugcgccc gcagccaug acaccaccca       480
cacaaucagg augggcccca uccacaagca cagucgcgag caccuugaaa guuaucagcg       540
cuguugagca gugcgcgagc uggcgccgug cggggggcagu ccagaagucc aggcccagau       600
ccgcagccau gcgguacgug cugaggguga agcucagcac cguagcggcc agccgcacgc       660
uguggcccac cgaagcccca uccaguagca gcacgaacag cggcac                     706
```

<210> SEQ ID NO 59
<211> LENGTH: 706
<212> TYPE: RNA
<213> ORGANISM: Chlamydomonas reinhardtii

<400> SEQUENCE: 59

```
gugccgcugc ucgugcugcu acuggauggg acuucggugg gccacagcgu gcggcuggcc        60
gcuacggugc ugagcuucac caacagcgcg uaccgcaugg cucugggucu gggccuggac       120
uucuggacug cccccacacg gcgccagcuc gcgcacugcu caacagcgcu gauaacuuuc       180
aaggugcucg cgacugugcu ugggauggg gcccauccug auugugggg uggugucaug       240
gcugcggggc gcacuguuug ccaucugggc agcagcccua uagcuaugcu caagcacauu       300
ggccagaaua gugucaagau guugcugacu uagcagagga uagcuccccc ggccacaacc       360
ccgcuauccu cugcuaaguc agcaacgucu ugacacugau cuggccaaug ugcuugagca       420
uagcuauagg gcugcugccc agauggcaaa cagugcgccc gcagccaug acaccaccca       480
cacaaucagg augggcccca uccacaagca cagucgcgag caccuugaaa guuaucagcg       540
cuguugagca gugcgcgagc uggcgccgug cggggggcagu ccagaagucc aggcccagau       600
ccgcagccau gcgguacgug cugaggguga agcucagcac cguagcggcc agccgcacgc       660
uguggcccac cgaagcccca uccaguagca gcacgaacag cggcac                     706
```

<210> SEQ ID NO 60

```
<211> LENGTH: 286
<212> TYPE: RNA
<213> ORGANISM: Chlamydomonas reinhardtii

<400> SEQUENCE: 60
cugcuuuagg acagacagua ucugugucgc ucaugcaagg dacagccaac gaauucccuc      60
gccacguuuu gggggcuugc acacuugcga guccguggcc cguguuuccaa ggauguauac    120
aagcgaaguc gagacuuugg uauuacauac ucccacuucg cuuuuauaca uucuuggaga    180
cacggccacg gacucgcagg ugugcaagcc cccgaaacgu cgccagggaa uucuuuggcu    240
gucccuugca ugagcgacac agauacagca aaggacuagc uagcag                   286

<210> SEQ ID NO 61
<211> LENGTH: 172
<212> TYPE: RNA
<213> ORGANISM: Chlamydomonas reinhardtii

<400> SEQUENCE: 61
cugugcgagu gguggccuac auacgguugg ugggcgugau cagcagggg aagcuuuauc       60
ggaauucgau gugcagggcg ugggcaca ugcccugcac aucgauuucc gauaaagcuu      120
cccccugcug aucacgccca ccaaccguau guaggccgcc gcgagagcgc ag             172

<210> SEQ ID NO 62
<211> LENGTH: 368
<212> TYPE: RNA
<213> ORGANISM: Chlamydomonas reinhardtii
<220> FEATURE:
<221> NAME/KEY: misc_feature
<222> LOCATION: (168)..(217)
<223> OTHER INFORMATION: n is a, c, g or u

<400> SEQUENCE: 62
uuguaacgac gggaaaaggc ccgcccuucg aaguuaucag gaacgggaag uacccacuua      60
ccuuacauuc uccgucaccu ucuccacguu cucgccgcgc agguacugca ggggcaucuc    120
gaugccauc gccucguagg cgcggagcuc aucaagcgcc ugcgucunnn nnnnnnnnn     180
nnnnnnnnnn nnnnnnnnnn nnnnnnnnnn nnnnnngca ggucgacucc gcggauccga    240
ggcgauggac aucgagaugc cccugcagua ccugcgcggc gagaacgcgg agaaggugc     300
ggagaaugua acgcggcggg uacuucccgu uccuggcaac uucuaagggc cuuucccgu    360
cguuacaa                                                             368

<210> SEQ ID NO 63
<211> LENGTH: 124
<212> TYPE: RNA
<213> ORGANISM: Chlamydomonas reinhardtii
<220> FEATURE:
<221> NAME/KEY: misc_feature
<222> LOCATION: (46)..(95)
<223> OTHER INFORMATION: n is a, c, g or u

<400> SEQUENCE: 63
uguaccgcug auugcgcuca caggggcaug agcucuggcu ggcaunnnnn nnnnnnnnn       60
nnnnnnnnnn nnnnnnnnnn nnnnnnnnnn nnnnnaugcc ccugugagcg caaucagcgg    120
uaca                                                                 124

<210> SEQ ID NO 64
<211> LENGTH: 98
<212> TYPE: RNA
<213> ORGANISM: Chlamydomonas reinhardtii
```

<400> SEQUENCE: 64
guguucuuuc auguguacca aggacgugau ggcucgcagu cuuuguucu acguaaaaga        60 cugcuagcca ucacauccuu gguacacaug aaagaacc                               98

<210> SEQ ID NO 65
<211> LENGTH: 98
<212> TYPE: RNA
<213> ORGANISM: Chlamydomonas reinhardtii

<400> SEQUENCE: 65
guguucuuuc auguguacca aggacgugau ggcucgcagu cuuuguucu acguaaaaga        60 cugcuagcca ucacauccuu gguacacaug aaagaacc                               98

<210> SEQ ID NO 66
<211> LENGTH: 103
<212> TYPE: RNA
<213> ORGANISM: Chlamydomonas reinhardtii

<400> SEQUENCE: 66
uccaucgggg gugucggggg gauuggaugc gcaugcaaua acaacuugau gaguugauca        60
acaaguuguu uuucgccccc auccgaccc cgcgaucgga agu                         103

<210> SEQ ID NO 67
<211> LENGTH: 159
<212> TYPE: RNA
<213> ORGANISM: Chlamydomonas reinhardtii

<400> SEQUENCE: 67
acuuugagca acauagggc uuuuuggaag ggagaacggu ggucaaacgg ugaagcgcgc        60
gcugcgcgaa gcaacuccga agcuaggggg gcgaggacgc aaacagugug gacucagagu       120
ccacccuucu cccuuccgaa aagcccuaug uuugcucaa                             159

<210> SEQ ID NO 68
<211> LENGTH: 318
<212> TYPE: RNA
<213> ORGANISM: Chlamydomonas reinhardtii
<220> FEATURE:
<221> NAME/KEY: misc_feature
<222> LOCATION: (119)..(206)
<223> OTHER INFORMATION: n is a, c, g or u

<400> SEQUENCE: 68
gcuggcagca gccaggcagg cagccgccgc cugaugagcu agacggcugg agggcgcaag        60
cacgcaacga ggggaugacg agcacgaugc gggccugaua cagccucguc gcccgccunn       120
nnnnnnnnnn nnnnnnnnnn nnnnnnnnnn nnnnnnnnnn nnnnnnnnnn nnnnnnnnnn       180
nnnnnnnnnn nnnnnnnnnn nnnnncccc gccuguauca ggcccacauc gugcucguca       240
uccccucguu gcgugcuugc gcccuccagc cgucuagccg ucaggagcug ugagccugcc      300
gcuggcgaug uggcuggc                                                    318

<210> SEQ ID NO 69
<211> LENGTH: 304
<212> TYPE: RNA
<213> ORGANISM: Chlamydomonas reinhardtii

<400> SEQUENCE: 69
gugggugggg gcgucgggcc cggccggggg cgcgugccgg ggcggugggc gcugaucguc        60

```
cugcugagcu ugcacucuuu ccaugcacgu accucuuauc cugcccuccc uccugcccua    120
uucuauuauc ccauaccaac uuauccaccu cucuuccggc uaccugccuu ugcccacagc    180
agacuacucg cgccgcaggg agggcuggau aagagguacg ugcaugguag gcgugccagc    240
ucugcaggac gauaagcgcu aaaggccacu ggaggugcag cugcgggccc gagcacuuac    300
ccau                                                                 304

<210> SEQ ID NO 70
<211> LENGTH: 62
<212> TYPE: RNA
<213> ORGANISM: Chlamydomonas reinhardtii

<400> SEQUENCE: 70
gguaggucag caugcgaccu agggaguagg agucggccuu ggggcccgag augcggccuu     60
cc                                                                    62

<210> SEQ ID NO 71
<211> LENGTH: 21
<212> TYPE: RNA
<213> ORGANISM: Chlamydomonas reinhardtii

<400> SEQUENCE: 71
aaggugugga ugcggcaugg g                                               21

<210> SEQ ID NO 72
<211> LENGTH: 21
<212> TYPE: RNA
<213> ORGANISM: Chlamydomonas reinhardtii

<400> SEQUENCE: 72
ugcgggaucc agugcugggg g                                               21

<210> SEQ ID NO 73
<211> LENGTH: 21
<212> TYPE: RNA
<213> ORGANISM: Chlamydomonas reinhardtii

<400> SEQUENCE: 73
ugcugggggu gucggcggag g                                               21

<210> SEQ ID NO 74
<211> LENGTH: 80
<212> TYPE: RNA
<213> ORGANISM: Chlamydomonas reinhardtii

<400> SEQUENCE: 74
cguggcaggg gucaaggugu ggaugcggca uggguggcua accccgccca ugcccagacc     60
acgcuccagc cccugccccg                                                 80

<210> SEQ ID NO 75
<211> LENGTH: 914
<212> TYPE: RNA
<213> ORGANISM: Chlamydomonas reinhardtii

<400> SEQUENCE: 75
acugccacuc ucaaggcggu cagcgaugcc cgcacgccgc caccgccgcc gucgccgaag     60
caggagaagc aaccagacca gcaacagcag uagcugcggu cgauguugac cgcacugcac    120
ggcaagccgc ugucgacgcg acugguugcc ucauggccug gcgguggagg cagcggguggu    180 agaggcgaca gcgcagcugc agccucuguu gugucugugc cggucagccg auugcuggcg    240
```

```
ccuaggcuag uggcggccgg gcugguggcg gccgggcugg uggcggcaag gcgggcgaug    300
uaggggaacu gccgccuuca aggcgcucug auccgcgcug gcgcggauca gagaagcaug    360
ugcgggaucc agugcugggg gugucggcgg aggcaggugg cgguggcggg gcgugugcgc    420
aucuacuugg ucccaaacga gcgaugcaag ugaagcugga aacgucuugc uuacaagagg    480
gggccagugu gauacgcauc aguccacggc aucaguccca aguagaugcg cacacgcccc    540
gccaccgcca ccugccuccg ccgacacccc cagcacugga uccgcacau gcugcucuga    600 uccgcgcuag cgcggaucag agcgccuuga aggcggcagu uccccuacau cgcccgccuu    660
gccaccacca gcccggccgc cacuagccua ggcgccagca aucggcugac cggcacagac    720
acaacagagg cugcagcugc gcugucgccu cuaccaccgc ugccuccacc gccaggccau    780
gaggcaacca gucgcgucga cagcggccuug ccgucagug cggucaacau cgaccgcugu    840
ugcugcuucu ccugcuucgg cgacggcggc ggguggcggcg ugcgggcauc gcugaccgcc    900
uugagagugg cagu                                                      914

<210> SEQ ID NO 76
<211> LENGTH: 18
<212> TYPE: DNA
<213> ORGANISM: Artificial sequence
<220> FEATURE:
<223> OTHER INFORMATION: Synthetic

<400> SEQUENCE: 76
tgcgggatcc agtgctgg                                                   18

<210> SEQ ID NO 77
<211> LENGTH: 22
<212> TYPE: DNA
<213> ORGANISM: Artificial sequence
<220> FEATURE:
<223> OTHER INFORMATION: Synthetic

<400> SEQUENCE: 77
gcgagcacag aattaatacg ac                                              22

<210> SEQ ID NO 78
<211> LENGTH: 110
<212> TYPE: DNA
<213> ORGANISM: Artificial sequence
<220> FEATURE:
<223> OTHER INFORMATION: Synthetic

<400> SEQUENCE: 78
catatggcgg ggccctgaca ccactgcggc cgtaggacgg ctagatccgg gaccgcgcct    60
ggacccgagg gaggaccccct cgggacccgg tacgtcgtcc cggatctagc              110

<210> SEQ ID NO 79
<211> LENGTH: 46
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (46)..(46)
<223> OTHER INFORMATION: n is a, c, g or t
<220> FEATURE:
<221> NAME/KEY: misc_feature
<222> LOCATION: (45)..(45)
<223> OTHER INFORMATION: v is a, c or g
```

<400> SEQUENCE: 79

```
gcgagcacag aattaatacg actcactatc ggttttttt ttttvn                    46
```

<210> SEQ ID NO 80
<211> LENGTH: 4356
<212> TYPE: DNA
<213> ORGANISM: Chlamydomonas reinhardtii

<400> SEQUENCE: 80

```
atgcacgcac catggccggc agcgactctc ccatggttgg gagatactgc acttgcaaaa    60
ggaccgcaag aagataactt actacggcat gttcacgtaa ctataagacg cattccggga   120
cctcgtggat gcagcaccgg cttctttgtc tacataactg catcatggct ttcggggcta   180
tggtacacga cagatcccct ggcgtacgcc gcgttgcggg cccaggtgcc aacactggtg   240
taccagatga gctcgacggc gttcttcaca gcgttggtgc tgaacttgac ctcgctcttg   300
ttcgaagaca acgcgccaaa acggcagctt gcgctgctca gctgcgccat caagggcgct   360
gcgtgtcaca cggacctact actggtcacc ggcgagcca cggtgctgta cgacgcgtac   420
ggctccatct gcataccgca gcgctacgtg cagtggctgg ttactacgcc caccatggtg   480
tatatcctgt caaagatatc cgacttcacg ccgcgccaga ccgccaccgc cattggtctg   540
gacgtgctga tggtgctgtc tggtctggtc gccaacttcc tgcggtcccc ctacctatgg   600
gtggccttcc tgacctccac ggcggccttc atcggcgtgc tgtacatgat gggcctcatg   660
gtctactcgg ccgtcaagga gcacaccagc gccaactccc gccgcagcct gctgttcatc   720
tacatgtgca cgttgttcat ctggaacctg tttcccctgg actggatcct gcacgtggtg   780
caccgcggct cgccggccgc cgagtaccta aacgttttcg ccaacttcat ggccaaggtg   840
ctgttcagct cctccatcat gtacggcaac tacatgacca ttgcgcagcg gcggctgctg   900
gcgcagcagg acgcggagaa cgccaaccgc gtgcagatga tccaggacct cgtgacagc    960
gtgacgcgca aggaccagtt catgagcttg atgagtcacg agctgcggac gccgctcaac  1020
ggcatcatcc agctgtcaga tgcgctggtc cggggtgcgg gcggcgagat gaaccccaag  1080
gggcagcact ttgtcaggac catcaagaac agctccaacc accttctcaa catcatcaac  1140
gacatcctgg atgtggcagc gctcaaggag gcaagctga ccatcaagca cgaggtgtgc   1200
tcgctggcca aggcggtgga ccacgtggtg acattgtgg cgccgctggc aaagaaggag  1260
gtgaccatgg agcgctgggt ggaccccgcc acgccgctca tcatcgccga cttcagccga  1320
gtcatccaga tcctgtacaa cctgaccggc aacgcgctca gttcacgaa caagggccgc   1380
gtgggcgtgc gcgtggagcc cagcgcggac ggcacacacg tgctgctgca ggtggacatg  1440
tcggtgacgc gcaagtacgg cggcacgggg ctgggcctca catcgtgaa gcagctggtg   1500
gaggcacacg agggaaccat tgaggtggcc agtgtggagg gccgcggcac caccttcact  1560
gtggagctgc cggtcctgca gagcagcacg cgccgcagcc tggaggggca ggtgctggac  1620
agcctgacgc gtctggagga cacgatcacg cagttcgccc gcggcgtgca gcggcgagcc  1680
agcgggctgc tggggcgcct gctgttcccc aaaatggcct accgtctacc acaaatgatg  1740
aatgtgctgt ctgtggacga cgaagacatc aaccagattg tcctggagga gatcctgacc  1800
gacagcggct acgcctttgc gcgctgcatg gatggcgccg aggcgctgga gtggctgtgc  1860
gcctccgaca ccatgcccga cctcatcctg ctggactgca tgatgccgt catgagcggg   1920
cacgagttct cgccacgct gagaaaggtg atcccgggca acgtgctccc ggttatcatg  1980
gtgagcgcca agagcgacga ggagaacatc gtggaggggc tgcgcagcgg ctccaacgac  2040
```

```
tttctggtga acaacgtgga cgggcgcgag acggagtcca tgaagctgct caagaacatc    2100
ctgcccgaga gcatcatcgc gcgcatgcag cagggccaga agtttgtggc cgacagccac    2160
ggccacgtcg tcatcctgtt ctcggacatc gttggcttca cctccctgtc ctccaagctg    2220
cccaccgccg aggtcttcct catgctctcc aacatgttca ccgcgtttga caagctcaca    2280
gaccgcttca gcgtctacaa ggtggagacc attggcgacg cctacatggt ggctgccggg    2340
cacgacgaag acgaggacaa ggaggccaag ggcagcccgc tcatgcgtgt gttgggcttc    2400
gcccgcgcca tgctggatgt ggtccgcaac atcaccgcgc caacggcga gcgcctgcgc     2460 atacgcatcg gcgtgcactg cggcccggcc tttgcgggcg tgatcggcat gaagtgcccg    2520
cgctactgct tcctgggcga caccgtcaac accgccagcc gcatggagag caccggcttc    2580
cccatgtgca tccacgtcag cgagaacgtg ttcaagcacc accccgccgc cgaggccgaa    2640
ctgcaggagg tgggggagcg cgacatcaag ggcaagggcc acatgcgcac ctacgtgcac    2700
gcgccgtctg cggcaggcgc tgtgatgggc agctcgcccg ctgcggcgct gcagctgttg    2760
ctgagcccca acagcgccgg cctgcactcg gggcacgcca acaccactct tgcctatctg    2820
gagcagcgca ttgccagctt aggcacgcag ctcgctaccg aggccctgtc taggcaacgc    2880
ctgcaggacg agctggacgc ggagcggcgg cgcgccgccg ttgcgtcgct gcgggccgcc    2940
ggtggcgcga atgagctctt gcctacgtcg aacgaagcca acagcaacgc cgacgctgac    3000
gtcatcattg gcggcggcgg catgtcgagc actgtagtgc cggcggcgca gccgccatcg    3060
tcctctgcct ttggcagcgc tggcgccgcc acctctggag gcagcggcaa tgacgaccag    3120
gagatcacgc tggcctcgcc gttcgtgtca gatctgcccg cgtatgctct ggaggctggg    3180
gacccgccga aggcgcagca gctacagcca ggcagccagt cgaccgcttt tgtggaagcg    3240
ggcggcgtcg gccgcagcgg cgcgagcggc ggcggcattg cggagccact gccgggctcg    3300
gcggctgagg cgtactcggg ctacagccgt cagcagctgg aggaccagct gctactgccg    3360
ccgctgcagc tacagccacc gccgctgccg tgctacagcc ttgacgctct ctttgtggat    3420
ctgggtctgg agccgtacct gccgcgtttc cgtgacgagg ccatccggct cgacatgctc    3480
ttgtccatgg acgcgcagca actggagcgg ctaggtctca gccgctgggg ctaccgcatc    3540
cgcgtgcgtg aggcggtggt ggagctggcg cggggcctgc tgcgctccac tgcaggcgtg    3600
tcagtagtgc actggtgtcg ggtgcccgtg tcaggcggcg gggcagcagc tgttgctgct    3660
gcgtcagggt gacggaaaag aaatgtgcaa tgcgtgtaaa aaagtgcgaa cctgggtagg    3720
aggcgcggcc ttgcaggagg gtggcagcga gctggcggct gccgctgctc ccaggcaggc    3780
aaacaatggg aaggatcggg aaacggccga gcggtggtgg tgtgacactt ttttggaatg    3840
caggttcgga ggtattcgga ggtactgtga tgcttcgggt ggaatctaat tgggatggcc    3900
acttgaccat tgcggtggac gatggaactt aagtaggctt ggaacgatgt gccttgagag    3960
caatcaaacc tcacacacag agagcatcag ccatgcgtgc gcgtgcgtgc tatgtaggtt    4020
tgcgggccgt ctgggggtca gtgggtggtg gggaagccat tgtgaggtcc ggtcgcaaga    4080
gcctggaagc gtgagcaacc gtgtcacttt gataacttgc tgcatcctac actgtggtgc    4140
cggagtggtc aagggaccgc tgcggcgcg tgggcacac agtgtgtgac caaactgcgc      4200
atttgagtca ttgtgcaccg tacagggttg ttccttggct cgtggcacca cttctccggc    4260
cacgaagctt gatggtgcgc gctgtgaccc atctacgggc gtgtcagggg aggcgcgagc    4320
atgatagtgt tgattttgac gacacgcgac acgctc                              4356
```

```
<210> SEQ ID NO 81
<211> LENGTH: 19
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (19)..(19)
<223> OTHER INFORMATION: v is a, c or g

<400> SEQUENCE: 81
tttttttttt tttttttv                                                   19

<210> SEQ ID NO 82
<211> LENGTH: 20
<212> TYPE: DNA
<213> ORGANISM: Artificial sequence
<220> FEATURE:
<223> OTHER INFORMATION: Synthetic

<400> SEQUENCE: 82
atgatgggcc tcatggtcta                                                 20

<210> SEQ ID NO 83
<211> LENGTH: 20
<212> TYPE: DNA
<213> ORGANISM: Artificial sequence
<220> FEATURE:
<223> OTHER INFORMATION: Synthetic

<400> SEQUENCE: 83
ccaggatgtc gttgatgatg                                                 20

<210> SEQ ID NO 84
<211> LENGTH: 20
<212> TYPE: RNA
<213> ORGANISM: Chlamydomonas reinhardtii

<400> SEQUENCE: 84
uguuggcucu gauucccuca                                                 20

<210> SEQ ID NO 85
<211> LENGTH: 289
<212> TYPE: RNA
<213> ORGANISM: Chlamydomonas reinhardtii

<400> SEQUENCE: 85
guagcagccg ggaccgcaga uagaggauau aggucgcgug agagagcggc ugacgccguc     60
uccauuccga uccuagacag guagucuuug accgcccuau gugagggaau cagagccaac   120
auguagccag gucuugauug ucuagugaug aucaagaccu ggcuacaugu uggcucugau   180
ucccucacau agggcgggcg aagacuaccu gucuaggauc ggaauggaga cggcgucagc   240
cgcucucuca cgcgaccuau auccucuauc ugcgggucgc ggcugcuac               289

<210> SEQ ID NO 86
<211> LENGTH: 1404
<212> TYPE: DNA
<213> ORGANISM: Artificial sequence
<220> FEATURE:
<223> OTHER INFORMATION: Synthetic

<400> SEQUENCE: 86
atgaagccca cgtcgactgc ctcgctgtcg ctttggaacg gctttgatga gtttacaccc    60
```

-continued

```
ctcaatgatc gagtggatgc accgccgctg tcgctaccgg ccatatccga gccgatgcgc       120
gtgattattg ttcggcatgg ccagtccact tggaacgccg agggccgcat ccagggcagc       180
accgacctct cggtcctcac agagaagggt gtgaagcagg caggcaagac acgcgacatg       240
ctttcggcag tgcccttctc cgcggtattc caaagcccac tggcccgcgc tcgccagacc       300
gcagacgtgg tgcttcaggg ccgccaccag ggggaaagcg cgcggcagtc gccaccggcc       360
accgcgccgc cttcgccgcc gccgccgcgg gtcacgctgc cctgcttgcg cgaggtggac       420
ctgtaccagt tccagggcct gctcaaggcc gaggggaagg cgctgtacgg cgaggcatac       480
atgcggtggc agcgcgcgcc tcacacattc gagatggacg gcagggcgcc ggtcagggag       540
ctgtggtacc gcggctctct ggcctggcaa agcctgctgc agcccccagcc tgctacagcc      600 tccgaagccg gcagtagcag cagcggtagc agtagcagca gcagcaatgg cggtggcggc       660
gctgcgggcg gcgctccggc gcgtcagctg ctggtggtgg cgcacaacgc catcaaccag       720
gggctggtgg cgacgcgct gggcctgcca ccgcagtact tcaggcgcct gccccagaac        780
aacgccgcac tcagtgtgct ggacttcaca cccgccacgg cgacggggtc ggcgcctcac       840
gtgaccctca gctgcctcaa ccagtcaccc gacaacccct tcaagaaccc ggacaaggtg       900
gtggggcacg ttgtgctgct gtcgccgccg gcggggggcg gcgagcagca ggcggcggcg       960
ctgcaagcgt tggcggctgt gttgagcaat ctgcaggtca cgcacgtgct aatggccacg      1020
cccgacgtca actcctacct cgtcacatcg ctgctcgcga cacagcagca acagccaacc      1080
gccgccgccg ccgccgccgc acccgtggag cacatgccgg cagccggccc ggaggtctgg      1140
cggcgcgccg tcgagctggc ggcggttaaa accggcggcg caaccaccgg ctcggccgta      1200
cagtacggca acgtgctcgt tctgctggac gagcagtcac acgcggcggc ggtgtgggcg      1260
gctctggggc tggcggcgcc gccggccgga gccgggccat tactccgagt gtcgccgggt      1320
gggctgtcgg tgtgtgagtt tgcggcggac ccggcccaga cgcctgcgac tgtgcgctgt      1380
atcaacaaca ccgcccactt gtag                                             1404
```

<210> SEQ ID NO 87
<211> LENGTH: 2763
<212> TYPE: DNA
<213> ORGANISM: Artificial sequence
<220> FEATURE:
<223> OTHER INFORMATION: Synthetic

<400> SEQUENCE: 87

```
atgggcaagg aggcccccgc tatcggtatt gacctgggca ccacgtacag ctgcgtgggt        60
gtctggcaga tgaccgcgt ggagattatt gccaacgatc agggcaaccg caccactccc       120
tcgtacgtgg ccttcacgga cactgagcgt ctgattggtg atgccgccaa gaaccaggtc       180
gctatgaacc gcgccacac ggtgttcgac gccaagcgcc tgattggccg caagttctcg       240
gaccccattg tccaggcgga cattaagctg tggcctttcc aggttcgcgc cggcgcgcac       300
gatgtgcccg agatcgttgt ctcctacaag aacgaggaga aggtcttcaa ggctgaggag       360
atctcctcga tggtgcttat caagatgaag gagaccgctc aggctttcct gggcgctgac       420
cgcgaggtca agaaggccgt ggtgaccgtg cccgcctact tcaacgactc ccagcgccag       480
gccaccaagg atgccggtat gattgccggc ctggaggtgc tgcgcatcat caacgagccc       540
accgccgccg ccattgccta cggcctggac aagaaggaca cgccggtgcg gagcgcaac      600 gtgctcatct tcgacctggg cggcggcacc ttcgatgtgt cgctgctgac cattgaggag       660
```

```
ggcatcttcg aggtcaaggc cactgccggt gacacccatc tgggcggtga ggacttcgac    720
gagcgcctgg tcaaccactt cgccaacgag ttccagcgca agtacaagaa ggacctgaag    780
acctcgcccc gtgctctgcg ccgcctgcgc accgcctgcg agcgcgctaa gcgcacgctg    840
tctagcgccg cgcagaccac catcgagctg actccctgt  tcgagggcgt ggacttcgcc    900
acctccatca cccgcgcccg cttgaggag  ctgtgcatgg acctgttccg caagtgcatg    960
gaccccgtgg agaagtgcct gcgcgacgcc aagatggaca gatgactgt  gcacgacgtg   1020
gtgctggtgg gcggctccac ccgtatcccc aaggtgcagc agctgctgca ggacttcttc   1080
aacggcaagg agctgaacaa gtcgatcaac cccgacgagg ccgtggccta cggcgccgcc   1140
gtgcaggccg ccattctgac cggcgagggc ggcgagaagg tgcaggacct gctgctgctg   1200
gacgtgacgc ccctgtcgct gggtctggag accgccggcg gcgtcatgac cgtgctcatc   1260
ccccgcaaca ccaccatccc caccaagaag gagcaggtgt tctcgaccta ctccgacaac   1320
cagcccggcg tgctgatcca ggtctacgag ggcgagcgcg cgcgcaccaa ggacaacaac   1380
ctgctgggca agttcgagct gaccggcatc ccgccgcgc  ctcgcggtgt gccccagatc   1440
aacgtgatct tcgacattga cgccaacggt atcctgaacg tgtctgccga ggacaagacc   1500
accggcaaca agaacaagat cacgatcacc aacgacaagg ccgcctgtc  caaggacgag   1560
atcgagcgca tggtgcagga ggcggagaag tacaaggctg acgacagca  gctgaagaag   1620
aaggtggagg ccaagaactc gctggagaac tacgcctaca acatgcgcaa caccatccgc   1680
gaggacaagg tggccagcca gctgtccgcc tcggacaagg agtcgatgga aaggcgctg    1740
accgccgcca tggactggct ggaggccaac cagatggccg aggtggagga gttcgagcac   1800
cacctcaagg agctggaggg cgtgtgcaac cccatcatca cccgcctcta ccagggcggc   1860
gccgcgcgcg gcggcatgcc cggcggcgcg cccggcgccg gcgctgcccc ctcgggcggc   1920
tcgggtgccg gccccaagat cgaggaggtc gactaatcgg cttcgcccca gactgaggag   1980
tgcgggaggc gccggcgggt ttgacggctg gcgccgtgga ctgggtgtgt gggtgcgccg   2040
gttgggcggc tgtggcgcgg cctagggccc ggacgtgggc cgggcgctgt attgatgtgt   2100
gggaacggca gacgccgctg tgcgttgtgt gtgaatacgt acctatatgc ccggcggcgc   2160
tgtagcactg atgctgtgtt tcgcgcgtgt cttgtgctcc ttgtgtttaa caacctggtt   2220
ggattgggac acccgcacgg tctacatact cagagcagga ctgagctgat tggtcggtcg   2280
gccggcgatt gattttgcca acatgcgctg aagtgcagcg ttgagttcgg actacgtggg   2340
atttgtggtt gttagctaga taggccccgg gctgctatct gttgcgtagc ggcccgtggg   2400
agcgaacgcg actgaggctg tggctgcacg catccgggct gttgaatggc tagggtcgtg   2460
cgcggaaggc cgttgctgag ccatgccaag tagagtagga tgacgatgat gttataagaa   2520
accgagatgg cacctagctc caactgagtt gggtgcggcc ttaggggaga ggcgtgcagg   2580
caggtgcaag ttccaaagca tgagagtggt gagtgagagg cgggagtggt ggatggaagt   2640
gcatggaggg ggtctcgaca gaactcaacg gcccgtcacg acaattcga  agggcggacg   2700
gctggacgta gtcgctacgg acgctgcccc acattgggtg gtgtgtaaaa gcagaagatt   2760
ccg                                                                 2763

<210> SEQ ID NO 88
<211> LENGTH: 2595
<212> TYPE: DNA
<213> ORGANISM: Artificial sequence
<220> FEATURE:
<223> OTHER INFORMATION: Synthetic
```

<400> SEQUENCE: 88

| | | | | | |
|---|---|---|---|---|---|
| atggacctcc | ctccggagct | ggccgtgctg | gccgataaag | ttctgtcact | ttccccggtt | 60 |
| gtgctggtcg | cgctcggcag | cgcggtgctt | atccttgcgc | tggccgtggg | ccgggtgctc | 120 |
| ttcaacctgc | tgccgagcaa | gcgtcccccg | gtgtgggagg | gccttccctt | catcggcgga | 180 |
| cttctcaagt | tcactggggg | cccgtggaag | ctgcttgaga | cggctatgc | caagtttggc | 240 |
| gagtgcttta | cggtccccgt | cgcgcatcgt | cgcgtgacat | tcctcatcgg | ccccgaggtg | 300 |
| tcgccccact | tcttcaaggc | tggcgacgat | gagatgagcc | agtcggaggt | gtacgacttc | 360 |
| aacattccca | ccttcggccg | tggcgtcgtc | tttgatgtgg | agcagaaggt | ccgcacagag | 420 |
| caatttcgca | tgttcactga | ggcgctgacc | aagaaccgcc | tgaagtcgta | cgtgccccac | 480 |
| ttcaacaagg | aggccgagga | gtacttcgcc | aagtggggcg | agacgggcgt | tgttgatttc | 540 |
| aaggacgagt | tcagcaagct | cattacgctg | accgccgccc | gcacactgct | gggccgcgag | 600 |
| gtgcgcgagc | agctgtttga | tgaggtggcg | gacctgctgc | acggcctgga | tgagggcatg | 660 |
| gtgccgctgt | ccgtgttctt | ccctacgcc | cccatccccg | tgcacttcaa | gcgcgaccgg | 720 |
| tgccgcaagg | atctggcggc | gatctttgcc | aagattatcc | gcgcccgccg | cgagtcgggc | 780 |
| cgccgcgagg | aggacgtgct | gcagcagttc | atcgacgcca | ggtaccagaa | cgtgaacggt | 840 |
| ggccgcgcgc | taacggagga | ggagatcacg | ggcctgctga | tcgccgtgct | gttcgcgggc | 900 |
| cagcacacca | gctccattac | cacctcgtgg | accggcatct | tcatggccgc | caacaaggag | 960 |
| cactacaaca | aggcggctga | ggagcagcag | gacatcatca | ggaagtttgg | caacgagctg | 1020 |
| tcgttcgaga | cgctgagcga | gatggaggtg | ctgcaccgca | catcaccga | ggcactgcgc | 1080 |
| atgcacccgc | cgttgctgct | ggtgatgcgc | tacgccaaga | agccgttctc | cgtgaccacc | 1140 |
| agcaccggga | agagctacgt | cattcccaag | ggcgacgtgg | tggcggcctc | gcccaacttc | 1200 |
| tcgcacatgc | tgccccagtg | cttcaacaac | cccaaggcct | acgacccccga | ccgctttgcg | 1260 |
| ccgccgcgcg | aggagcagaa | caagccctac | gccttcatcg | ggttcggcgc | cggccgccac | 1320 |
| gcctgcatcg | gccagaactt | cgcctacctg | cagatcaagt | ccatctggtc | ggtgttgctg | 1380 |
| cgcaacttcg | agtttgagct | gctggacccc | gtgccggagg | ctgactacga | gtccatggtg | 1440 |
| atcgggccca | agccatgccg | cgtgcgctac | acgcgccgca | agctgtaagc | tggccgttgc | 1500 |
| agttcgggtg | gcttatcagt | cgtcccttta | ggtctccctg | taaggaggtc | gaggagacca | 1560 |
| acatgaggtt | tgccgcccag | gggatgcggt | tgaggcggcg | gcatggcgat | atgtgaagag | 1620 |
| gggcgaggga | ggaagtgcat | gtgggctggt | ggtgcagagt | gtgtgaaagg | ttatgagcgc | 1680 |
| ggtcaggtac | atttactgtt | gtagacgtac | gtgaaggcgt | gcacatagtt | gcctaggcat | 1740 |
| gggtaacgca | agacaaggta | aggtcaggag | tgtactatat | ggagtcgccg | agcagactgc | 1800 |
| tggagcgggc | ttcatggcgg | acttgctcaa | tggctaagat | gttgcttgag | cacaagcctt | 1860 |
| tgcacgtgga | atactagatg | actgtcgcgg | gctaccagta | cctcgacgat | agtgactttg | 1920 |
| cagggagggg | tttatgtgac | taagggcacc | ttaagagtct | tcggtgtgta | tctggtctgc | 1980 |
| tatgcaagct | tcgtgccgtg | ggtgcgggcg | cgctgtggtt | cggcacgcca | ttttgacgtt | 2040 |
| tcacggcatg | cgcgggctgc | catacgctgg | cagatgtgtg | gggctgtgct | ggacttaagg | 2100 |
| gtctaggtag | tgcaacgatg | agtcgatgac | tttacagcaa | gcggtgcgct | ggccaaactg | 2160 |
| gcatataacg | tttggtgtac | acagcttaca | tgcacggctc | tggggcgcct | gggcgtactg | 2220 |
| gtgacagtga | cggagctggg | ccaatgggtg | acatgcgaat | gcagagcgga | gggaacaggc | 2280 |

```
acggccacaa ggagaccgtg caaagcggcg ccggggcaga ggataagggc tgccgggtgg    2340
cctgtgtctg tttgggggca cagcttttgc cagctgcttg cctttggggg gctgtgggcg    2400
atatgctgca tgctggactg agctgaacct ggatcgcggg ccctgccttc ttccgactgc    2460
tgggtcactc gtatctcttt gacagaaatc tgctcccaaa ggcctttgct gcctcaggct    2520
gccttgatct tgcattgaaa cacggtacct gtcaaggcgc ctgggtactc cacggccgtg    2580
taataacgtg caaaa                                                     2595
```

US 8,802,923 B2

COMPOSITIONS AND METHODS FOR ENHANCING OIL CONTENT IN PLANTS

CROSS-REFERENCE TO RELATED PATENT APPLICATIONS

This application is the U.S. National Phase of PCT/IL2009/000394, filed Apr. 7, 2009, which claims priority from U.S. Provisional Application Nos. 61/043,747, filed Apr. 10, 2008 and 61/159,092, filed Mar. 11, 2009, all of which are incorporated herein by reference in entirety.

FIELD OF THE INVENTION

The invention relates to microRNAs and related nucleic acid sequences associated with enhanced oil content in plants, as well as to methods for generating transgenic plants with enhanced oil content.

BACKGROUND OF THE INVENTION

Biofuel is defined as solid, liquid or gaseous fuel derived from relatively recently dead biological material (and is thereby distinguished from fossil fuels, which are derived from long dead biological material). Theoretically, biofuels can be produced from any (biological) carbon source; although, the most common sources are photosynthetic plants. Various plants and plant-derived materials are used for biofuel manufacturing. Agrofuels are biofuels which are produced from specific crops, rather than from waste processes.

There are two common strategies of producing liquid and gaseous agrofuels. One is to grow crops high in sugar (sugar cane, sugar beet, and sweet sorghum) or starch (corn/maize), and then use yeast fermentation to produce ethyl alcohol (ethanol). The second is to grow plants that contain high amounts of vegetable oil, such as oil palm, soybean, algae, jatropha, or pongamia pinnata. When these oils are heated, their viscosity is reduced, and they can be burned directly in a diesel engine, or they can be chemically processed to produce fuels such as biodiesel. Wood and its byproducts can also be converted into biofuels such as methanol or ethanol fuel.

Algae can be used as a source for several types of biofuels with the most studied one being biodiesel. Algae are fast-growing organisms with naturally high oil content that can be extracted year-round. Algae can be grown in non-arable areas and thus do not compete with food crops on land. Algae provide the most promising long-term solution for sustainable biofuels production with only a minimal cropping area required to supplement a large fuel supply. Interest in algae is recently growing as a potential feedstock for biodiesel production with the emerging concern about global warming that is associated with the increased usage of fossil fuels.

Algal biotechnology has made considerable advances in recent years including development of methods for genetic transformation and sequencing the genomes of several algal species and significant efforts have been made over the last 15 years to increase the oil yield in algae. Oil content in algae is known to be influenced by several environmental and nutritional factors such as nitrogen starvation and strong light. Although much has been learned about genetic control of oil synthesis in algae over that time, researchers have still not been able to significantly increase the oil yield of algae by genetic engineering.

MicroRNAs are 17-24 nucleotide long, endogenous RNAs that regulate gene expression in plants and animals. MicroRNAs are processed from stem-loop regions of long primary transcripts and are loaded into silencing complexes, where in plants they generally direct cleavage of complementary mRNAs. MicroRNAs play crucial roles at each major stage of plant development, typically at the cores of gene regulatory networks, usually targeting genes that are themselves regulators thus affecting the abundance or stability of numerous genes at once.

Recently, microRNAs have been discovered in the unicellular model alga *Chlamydomonas reinhardtii* and preliminary evidence indicates they play crucial roles in algal development (Molnar et al., 2007, Nature 447:1126-1130).

So far, plant microRNAs that target genes involved in abiotic and biotic stress responses, hormone signaling and metabolism and the microRNA machinery itself have been identified (Jones-Rhoades et al., 2006, Annu Rev Plant Biol 57:19-53).

A commonly-used approach in identifying the function of novel genes is through a loss-of-function mutant screening. In many cases, functional redundancy exists between genes that are members of the same family. When this happens, a mutation in one gene member might have a reduced or even non-existing phenotype and the mutant lines might not be identified in the screening.

Using microRNAs, multiple members of the same gene family can be silenced simultaneously, giving rise to much more intense phenotypes. This approach is also superior to RNA interference (RNAi) techniques where typically 100-800 bp fragments of the gene of interest form a fold-back structure when expressed. These long fold-back RNAs form many different small RNAs and prediction of small RNA targets other then the perfectly complementary intended targets are therefore very hard. MicroRNAs in contrast, are produced from precursors, which are normally processed such that preferentially one single stable small RNA is generated, thus significantly minimizing the "off-target" effect.

A second approach of functional screening is through overexpression of genes of interest and testing for their phenotypes. In many cases, attempting to overexpress a gene which is under microRNA regulation results in no significant increase in the gene's transcript. This can be overcome either by expressing a microRNA-resistant version of the gene or by downregulating the microRNA itself.

Attempts to increase oil yield in algae through standard molecular biology techniques was so far only marginally successful. In recent years, major effort was focused on studying the Acetyl-CoA carboxylase (ACCase) enzyme, which is considered to regulate a key step in fatty acid biosynthesis. While efforts focused on genetic manipulation to increase the activity of ACCase have been going on for at least 15 years, the research has not yet reached the stage of actually being able to substantially increase the net oil yield from algae.

There is an unmet need to efficiently introduce significant changes in plants traits such as oil content.

SUMMARY OF THE INVENTION

The present invention provides transgenic plants with altered oil content. The invention further provides nucleic acid sequences and methods for generating such plants.

According to one aspect, the present invention provides a transgenic plant transformed with an isolated nucleic acid selected from the group consisting of a microRNA, a microRNA precursor, a microRNA target, a microRNA-resistant target, a fragment thereof, a nucleic acid sequence capable of hybridizing thereto under stringent conditions, a nucleic acid sequence having at least 80% identity thereto, and combinations thereof, wherein modulated expression of the isolated nucleic acid sequence results in altered oil content in said transgenic plant compared to a corresponding wild type plant.

According to one embodiment, the nucleic acid sequence is selected from the group consisting of SEQ ID NOS: 14, 17, 35, 48, 51, 66, 78, 1-13, 15-16, 18-34, 36-47, 49-50, 52-65, 67-75, 80, 84 and 85, a complementary sequence thereof, a fragment thereof, a nucleic acid sequence capable of hybridizing thereto under stringent conditions, and sequences having at least 80% identity thereto, and wherein the alteration is increased oil content.

According to some embodiments the nucleic acid sequence is selected from the group consisting of SEQ ID NOS: 4, 6, 8, 12-15, 17, 20, 24-26, 29-31, 34-36, 41, 43, 44, 46-49, 51, 52, 55-57, 60-62, 65-67, 80, 84 and 85, a fragment thereof, a nucleic acid sequence capable of hybridizing thereto under stringent conditions and sequences having at least 80% identity thereto, wherein the modulated expression is upregulation of said nucleic acid sequence. According to some embodiments the transformation comprises introduction of said nucleic acid sequence into said plant.

Also provided is a transgenic plant transformed with an isolated nucleic acid selected from the group consisting of SEQ ID NOS: 14, 17, 35, 48, 51, 66 and 78, a fragment thereof, a nucleic acid sequence capable of hybridizing thereto under stringent conditions and sequences having at least 80% identity thereto, wherein the transformation comprises introduction of the nucleic acid sequence into the plant, and wherein the transformation results in enhanced oil content in said transgenic plant compared to a corresponding wild type plant.

According to some embodiments the transformation results in downregulated expression of a nucleic acid sequence selected from the group consisting of SEQ ID NOS: 1, 5, 9, 16, 21, 23, 27, 28, 32, 37-39, 40, 42, 45, 50, 53, 54, 58, 59, 63 and 68-75, a fragment thereof, a nucleic acid sequence capable of hybridizing thereto under stringent conditions and sequences having at least 80% identity thereto, and the alteration is increased oil content.

According to some embodiments, the transformation comprises introduction of a microRNA-resistant target of a nucleic acid sequence selected from the group consisting of SEQ ID NOS: 1, 5, 9, 16, 21, 23, 27, 28, 32, 37-39, 40, 42, 45, 50, 53, 54, 58, 59, 63 and 68-75, a fragment thereof, a nucleic acid sequence capable of hybridizing thereto under stringent conditions and sequences having at least 80% identity thereto into said plant. According to some embodiments, the sequence of the introduced microRNA-resistant target is selected from the group consisting of SEQ ID NOS: 86-88, a fragment thereof, a nucleic acid sequence capable of hybridizing thereto under stringent conditions and sequences having at least 80% identity thereto.

According to another aspect, the present invention provides a vector comprising a nucleic acid sequence associated with oil content of a plant, wherein said nucleic acid sequence is selected from the group consisting of a microRNA, a microRNA precursor, a microRNA target, a microRNA-resistant target, a fragment thereof, a nucleic acid sequence capable of hybridizing thereto and a nucleic acid sequence having at least 80% identity thereto.

According to some embodiments the nucleic acid sequence is selected from the group consisting of SEQ ID NOS: 4, 6, 8, 12-15, 17, 20, 24-26, 29-31, 34-36, 41, 43, 44, 46-49, 51, 52, 55-57, 60-62, 65-67, 80, 84 and 85, a fragment thereof, a nucleic acid sequence capable of hybridizing thereto and a nucleic acid sequence having at least 80% identity thereto.

According to other embodiments the sequence is a microRNA-resistant target of a sequence selected from the group consisting of SEQ ID NOS: 1, 5, 9, 16, 21, 23, 27, 28, 32, 37-39, 40, 42, 45, 50, 53, 54, 58, 59, 63 and 68-75, a fragment thereof, a nucleic acid sequence capable of hybridizing thereto and a nucleic acid sequence having at least 80% identity thereto. According to further embodiments the sequence of the microRNA-resistant target is selected from the group consisting of SEQ ID NOS: 86-88, a fragment thereof, a nucleic acid sequence capable of hybridizing thereto and a nucleic acid sequence having at least 80% identity thereto.

According to another aspect, the present invention provides a method for altering the oil content in a plant, comprising modulating, in said plant, the expression of a nucleic acid sequence selected from the group consisting of a microRNA, a microRNA precursor, a microRNA target, a microRNA-resistant target, a fragment thereof, a nucleic acid sequence capable of hybridizing thereto under stringent conditions, a nucleic acid sequence having at least 80% identity thereto and combinations thereof.

According to some embodiments the nucleic acid sequence is selected from the group consisting of SEQ ID NOS: 14, 17, 35, 48, 51, 66, 78, 1-13, 15-16, 18-34, 36-47, 49-50, 52-65, 67-75, 80, 84 and 85, a complementary sequence thereof, a fragment thereof, a nucleic acid sequence capable of hybridizing thereto under stringent conditions and a nucleic acid sequence having at least 80% identity thereto, and said alteration is increased oil content.

According to some embodiments the nucleic acid sequence is selected from the group consisting of SEQ ID NOS: 4, 6, 8, 12-15, 17, 20, 24-26, 29-31, 34-36, 41, 43, 44, 46-49, 51, 52, 55-57, 60-62, 65-67, 80, 84 and 85, a fragment thereof, a nucleic acid sequence capable of hybridizing thereto under stringent conditions and a nucleic acid sequence having at least 80% identity thereto, and the modulation comprises overexpressing said nucleic acid sequence by its introduction it into said plant.

Also provided in accordance with the invention is a method for enhancing the oil content in a plant, comprising introducing into said plant a nucleic acid sequence selected from the group consisting of SEQ ID NOS: SEQ ID NOS: 14, 17, 35, 48, 51, 66 and 78, a fragment thereof, a nucleic acid sequence capable of hybridizing thereto under stringent conditions and a nucleic acid sequence having at least 80% identity thereto, wherein expression of the introduced nucleic acids enhances the oil content in said plant.

According to some embodiments the modulation results in downregulated expression of a nucleic acid sequence is selected from the group consisting of SEQ ID NOS: SEQ ID NOS: 1, 5, 9, 16, 21, 23, 27, 28, 32, 37-39, 40, 42, 45, 50, 53, 54, 58, 59, 63 and 68-75, a fragment thereof, a nucleic acid sequence capable of hybridizing thereto under stringent conditions and a nucleic acid sequence having at least 80% identity thereto, and the alteration is increased oil content.

According to some embodiments the method comprises introducing a microRNA-resistant target of a nucleic acid sequence selected from the group consisting of SEQ ID NOS: SEQ ID NOS: 1, 5, 9, 16, 21, 23, 27, 28, 32, 37-39, 40, 42, 45, 50, 53, 54, 58, 59, 63 and 68-75, a fragment thereof, a nucleic acid sequence capable of hybridizing thereto under stringent conditions and a nucleic acid sequence having at least 80% identity thereto, and the alteration is increased oil content. According to further embodiments the sequence of the microRNA-resistant target is selected from the group consisting of SEQ ID NOS: 86-88, a fragment thereof, a nucleic acid sequence capable of hybridizing thereto under stringent conditions and a nucleic acid sequence having at least 80% identity thereto.

According to some embodiments of the invention, the expression of the introduced nucleic acid is driven by a promoter expressible in a plant cell selected from the group consisting of a constitutive, inducible, and tissue-specific promoter, operably linked to the nucleic acid.

According to some embodiments, the transgenic plant of the invention is selected from the group consisting of Corn, Rapeseed/Canola, Soybean, Sugarcane, sugar beet, Barley, Wheat, Jatropha, Castor bean, Chinese Tallow, Palm, Camelina, and Mustard. According to some embodiments the plant is algae. According to some embodiments the algae selected from the group consisting of *Neochloris oleoabundans, Scenedesmus dimorphus, Euglena gracilis, Phaeodactylum tricornutum, Pleurochrysis carterae, Tetraselmis chui, Tetraselmis suecica, Isochrysis galbana, Nannochloropsis salina, Nannochloropsis oculata, Botryococcus braunii, Dunaliella tertiolecta, Nannochloris* sp., *Spirulina* sp., *Chlorella* sp., *Crypthecodinium cohnii, Cylindrotheca* sp., *Dunaliella primolecta, Monallanthus salina, Nitzschia* sp., *Schizochytrium* sp. and *Tetraselmis sueica*. According to some embodiments the algae is selected from the group consisting of *Chlamydomonas reinhardtii, Chlorella vulgaris* and *Phaeodactylum tricornutum*.

According to another aspect, the invention provides a seed obtained from a transgenic plant of the invention. The invention further provides a seed obtained by use of a vector of the invention, and a seed obtained by use of a method of the invention.

These and other embodiments of the present invention will become apparent in conjunction with the figures, description and claims that follow.

BRIEF DESCRIPTION OF THE DRAWINGS

FIG. 2A shows results for line transformed with a sequence consisting of the mature microRNA sequence of CRMIR5 inserted in the cre-mir1162 backbone (CRMIR5 replacing mature cre-mR1162) (SEQ ID NO: 78).

FIG. 2B shows results for the line transformed with cre-mir1151b (SEQ ID NO: 48).

FIG. 2C shows results for the line transformed with cre-mir1157 (SEQ ID NO: 51).

FIG. 2D shows results for the line transformed with CRMIR121 (SEQ ID NO: 66).

FIG. 4A presents the differential expression of CRMIR137 (SEQ ID NO: 73) which is downregulated in nitrate-limiting conditions relative to nitrate-sufficient conditions with a p-value of 0.02 and a fold change of 1.9.

FIG. 4B presents the differential expression of cre-miR1142 (SEQ ID NO: 71) which is downregulated in nitrate-limiting conditions relative to nitrate-sufficient conditions with a p-value of 0.04 and a fold change of 1.6.

FIG. 4C presents the differential expression of cre-miR1167 (SEQ ID NO: 21) which is downregulated in nitrate-limiting conditions relative to nitrate-sufficient conditions with a p-value of 0.03 and a fold change of 1.6.

FIG. 4D presents the differential expression of CRMIR129 (SEQ ID NO: 37) which is downregulated in nitrate-limiting conditions relative to nitrate-sufficient conditions with a p-value of 0.02 and a fold change of 1.5.

FIG. 4E presents the differential expression of CRMIR136 (SEQ ID NO: 72) which is downregulated in nitrate-limiting conditions relative to nitrate-sufficient conditions with a p-value of 0.02 and a fold change of 1.5.

DETAILED DESCRIPTION OF THE INVENTION

Figure 1:
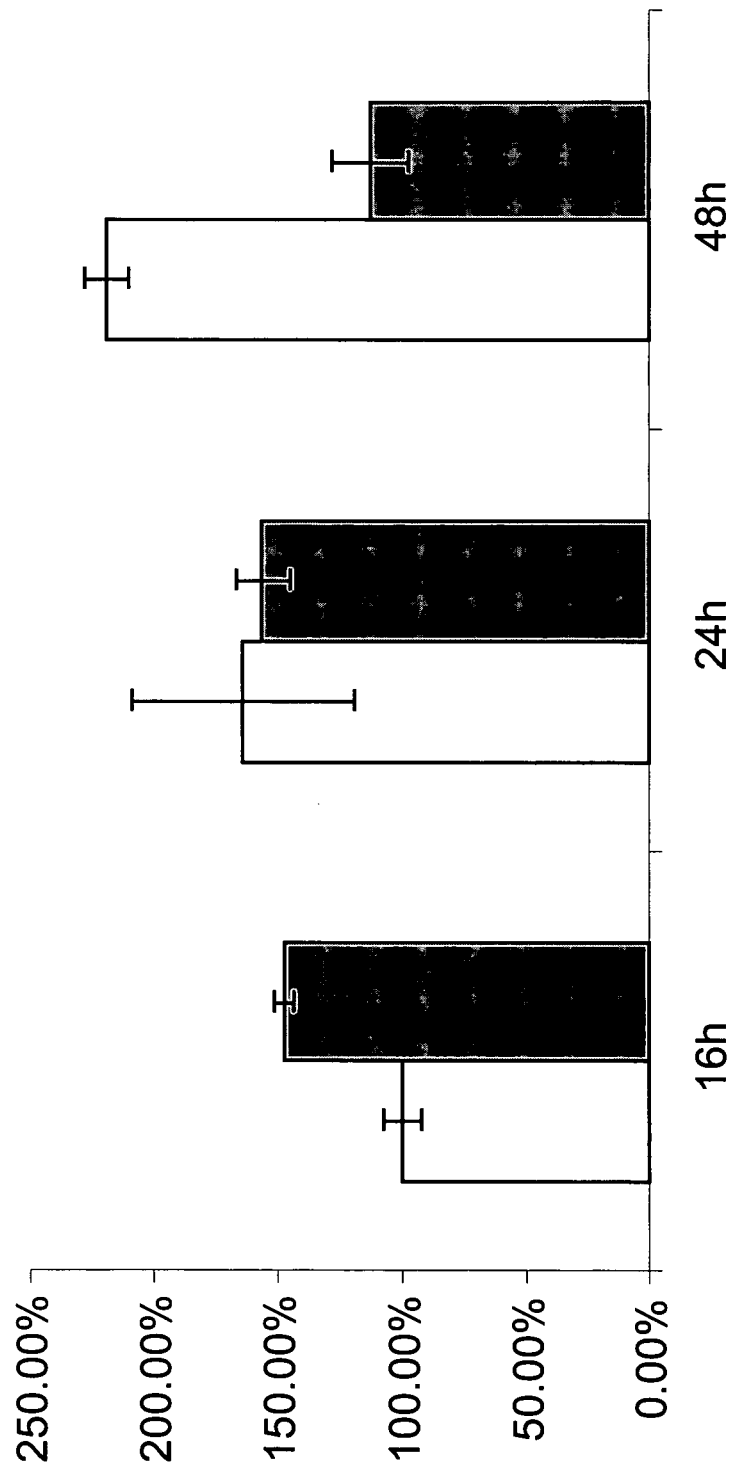
FIG. 1 shows oil content in *C. reinhardtii* in response to the nitrogen starvation and strong light inductions. The Y-axis represents the percent of oil content as compared to control and the X-axis represents the time of cell harvesting for oil content analysis. The white bars represent the strong-light induction, and the light gray bars represent the nitrogen starvation induction.
Figure 2A:
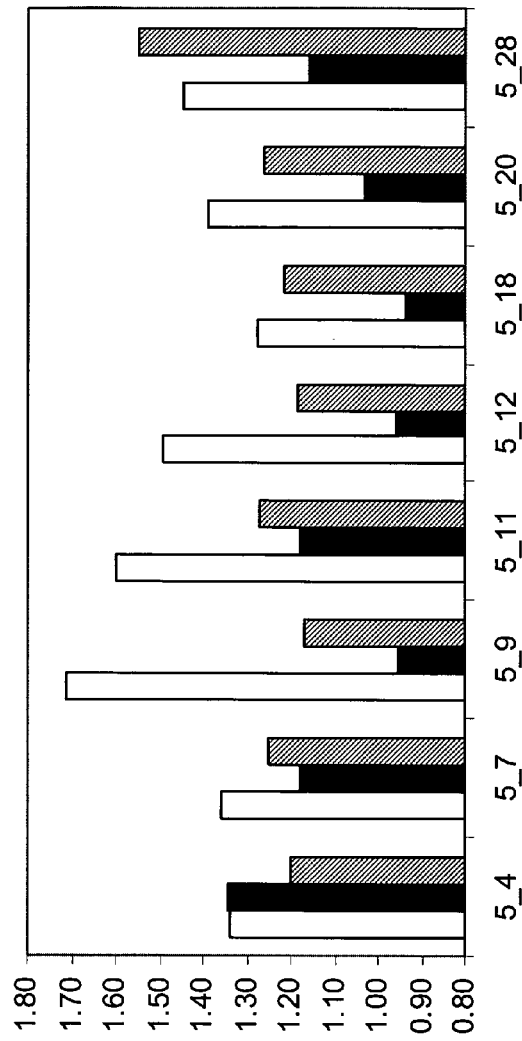
FIGS. 2A-2D show oil content in transformed lines of *C. reinhardtii* overexpressing different microRNAs. The Y-axis represents the oil content in the transformed lines relative to the oil content in the wild type line grown under the same conditions. The X-axis present groups of results for several clones of each line, each clone designated with a number. The black and white bars represent experiments preformed in 50 ml tubes containing 10 ml of TAP growth medium, and the diagonally-striped bars represent experiments preformed in 250 ml flasks containing 50 ml of TAP growth medium.
Figure 2B:
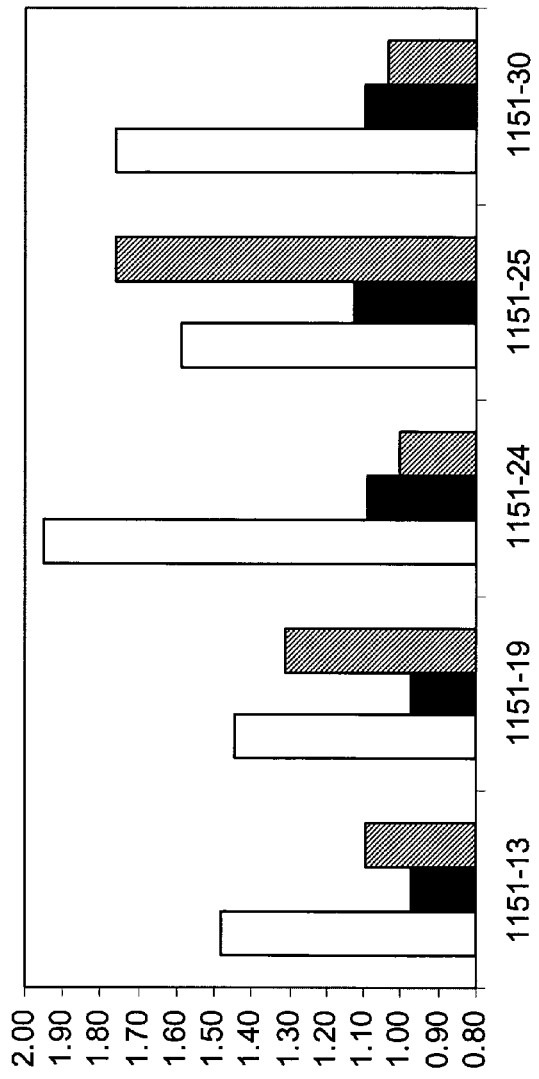
Figure 2C:
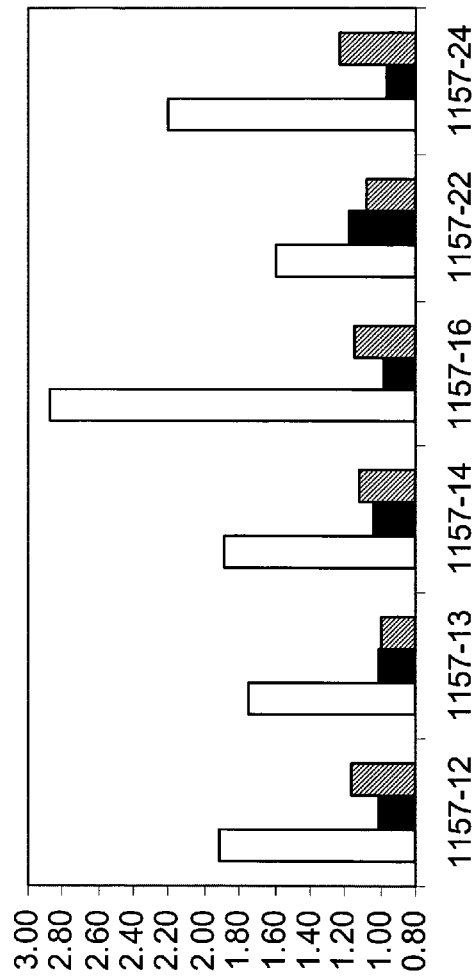
Figure 2D:
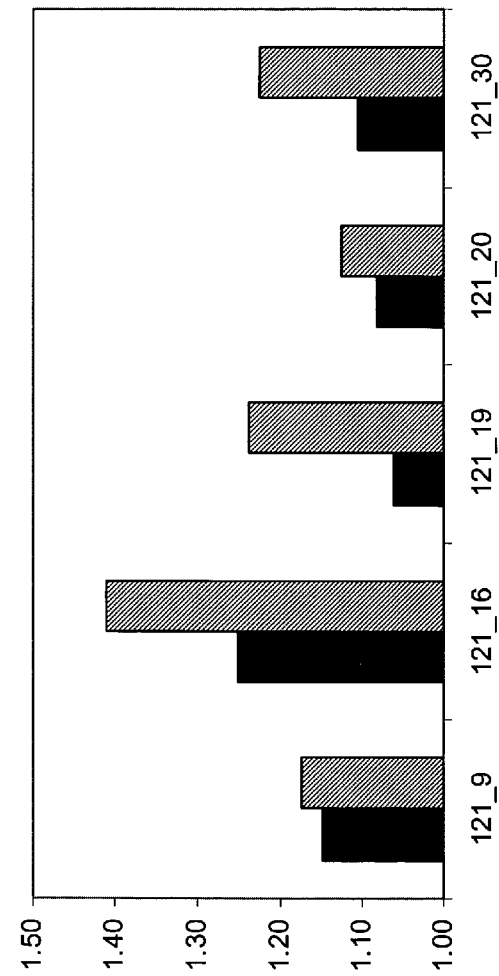

According to some aspects of the present invention, oil production was induced in algae by nitrogen starvation and strong light, and isolated nucleic acid sequences, including microRNAs and microRNA precursors, associated with oil synthesis were identified. Additionally, lines of *C. reinhardtii* transformed to overexpress microRNA precursors associated with oil synthesis were found to have increased oil content relative to controls.

Before the present compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9 and 7.0 are explicitly contemplated.

1. General Definitions

About

As used herein, the term "about" refers to +/−10%.

Algae

Algae include organisms that belong to the phyla *Chlorophyta* (green algae), *Eustigmatophyceae* (eustigmatophytes), *Phaeophyceae* (brown algae), *Bacillariophyta* (diatoms), *Xanthophyceae* (yellow-green algae), *Haptophyceae* (prymnesiophytes), *Chrysophyceae* (golden algae), *Rhodophyta* (red algae) and *Cyanobacteria*, (blue-green algae). Specific examples of algae include, but are not limited to, *Neochloris oleoabundans, Scenedesmus dimorphus, Euglena gracilis, Phaeodactylum tricornutum, Pleurochrysis carterae, Tetraselmis chui, Tetraselmis suecica, Isochrysis galbana, Nannochloropsis salina, Botryococcus braunii, Dunaliella tertiolecta, Nannochloris* sp., *Spirulina* sp., *Chlorella* sp., *Crypthecodinium cohnii, Cylindrotheca* sp., *Dunaliella primolecta, Monallanthus salina, Nitzschia* sp., *Schizochytrium* sp. and *Tetraselmis sueica*.

Auxotrophy

As used herein, auxotrophy is the inability of an organism to synthesize a particular organic compound required for its growth.

Binding Site

As used herein, the term "binding site" may comprise a target nucleic acid or a portion thereof. The binding site has a perfect or near-perfect complementarity to one of the miRNA sequences as listed in Sanger database, version 10.1 or the database of Molnar et al, 2007.

Biodiesel

As used herein, the term "Biodiesel" refers to a non-petroleum-based diesel fuel consisting of long-chain alkyl (methyl, propyl or ethyl) esters. Biodiesel is made by chemically-reacting lipids, typically vegetable oil or animal fat, and alcohol. It can be used (alone, or blended with conventional petrodiesel) in unmodified diesel-engines.

Complement

"Complement" or "complementary" as used herein to refer to a nucleic acid may mean Watson-Crick or Hoogsteen base pairing between nucleotides or nucleotide analogs of nucleic acid molecules. A full complement or fully complementary means 100% complementary base pairing between nucleotides or nucleotide analogs of nucleic acid molecules.

Differential Expression

"Differential expression" means qualitative or quantitative differences in the temporal and/or spatial gene expression patterns within and among cells and tissue. Thus, a differentially expressed gene may qualitatively have its expression altered, including an activation or inactivation, in, e.g., standard conditions versus environmental or nutritional stress. Genes may be turned on or turned off in a particular state, relative to another state thus permitting comparison of two or more states. A qualitatively regulated gene may exhibit an expression pattern within a state or cell type which may be detectable by standard techniques. Some genes may be expressed in one state or cell type, but not in both. Alternatively, the difference in expression may be quantitative, e.g., in that expression is modulated, up-regulated, resulting in an increased amount of transcript, or down-regulated, resulting in a decreased amount of transcript. The degree to which expression differs needs only be large enough to quantify via standard characterization techniques such as expression arrays, quantitative reverse transcriptase PCR, Northern blot analysis, real-time PCR, in situ hybridization and RNAse protection.

Expression Profile

The term "expression profile" is used broadly to include a genomic expression profile, e.g., an expression profile of microRNAs. Profiles may be generated by any convenient means for determining a level of a nucleic acid sequence e.g. quantitative hybridization of microRNA, labeled microRNA, amplified microRNA, cDNA, etc., quantitative PCR, ELISA for quantification, and the like, and allow the analysis of differential gene expression between two samples. Samples are collected by any convenient method, as known in the art. Nucleic acid sequences of interest are nucleic acid sequences that are found to be predictive, including the nucleic acid sequences provided below, where the expression profile may include expression data for 5, 10, 20, 25, 50 or more of, including all of the listed nucleic acid sequences. According to some embodiments, the term "expression profile" means measuring the abundance of the nucleic acid sequences in the measured samples.

Feedstock

Feedstocks refer to the crops or products that can be used as or converted into biofuels and bioenergy. Each feedstock has advantages and disadvantages in terms of how much usable material they yield, where they can grow and how energy and water-intensive they are. As used herein, second generation feedstocks refers broadly to crops that have high potential yields of biofuels, but that are not widely cultivated, or not cultivated as an energy crop.

Gene

"Gene" as used herein may be a natural (e.g., genomic) or synthetic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA or antisense RNA. A gene may also be an mRNA or cDNA corresponding to the coding regions (e.g., exons) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto.

Identity

"Identical" or "identity" as used herein in the context of two or more nucleic acids or polypeptide sequences mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA sequences, thymine (T) and uracil (U) may be considered equivalent. Identity may be performed manually or by using a computer sequence algorithm such as BLAST or BLAST 2.0.

MicroRNA-Resistant Target

As used herein, "microRNA-resistant target" is a microRNA target modified such that the microRNA cannot bind and microRNA mediated target regulation is therefore prevented.

Modulated (or: Modified) Expression

As used herein, modulated expression in reference to a nucleic acid sequence indicates that the pattern of expression in, e.g., a transgenic plant or plant tissue, is different from the expression pattern in a wild-type plant or a reference plant of the same species. The pattern of expression may also be compared with a reference expression pattern in a wild-type plant of the same species. For example, the nucleic acid is expressed in a cell or tissue type other than a cell or tissue type in which the sequence is expressed in the wild-type plant, or by expression at a time other than at the time the sequence is expressed in the wild-type plant, or by a response to different inducible agents, such as hormones or environmental signals, or at different expression levels (either higher or lower) compared with those found in a wild-type plant. The term also refers to modulated expression patterns that are produced by lowering the levels of expression to below the detection level or completely abolishing expression. The resulting expression pattern can be transient or stable, constitutive or inducible. The modulated expression may be of either or both of an endogenous nucleic acid, or an exogenous nucleic acid introduced to the plant.

Overexpression

The term "overexpression" as used herein refers to a greater expression level of a gene in a plant, plant cell or plant tissue, compared to expression in a wild-type plant, cell or tissue, at any developmental or temporal stage for the gene. Overexpression can occur when, for example, the genes encoding one or more genes or transcription factors are under the control of a strong expression signal. Overexpression may occur throughout a plant or in specific tissues of the plant, depending on the promoter used. Overexpression results in a greater than normal production, or "overproduction" of a gene product in a plant, cell or tissue.

Plant

Plants include anything under the kingdom "Viridiplantae", e.g. Corn, Rapeseed/Canola, Soybean, Sugarcane, sugar beet, Barley, Wheat, Jatropha, Castor bean, Chinese Tallow, Palm, and Mustard. Plants also include Green algae, and as used herein, plants further include algae that belong to the phyla Eustigmatophyceae (eustigmatophytes), Phaeophyceae (brown algae), Bacillariophyta (diatoms), Xanthophyceae (yellow-green algae), Haptophyceae (prymnesiophytes), Chrysophyceae (golden algae), Rhodophyta (red algae) and Cyanobacteria, (blue-green algae).

Probe

"Probe" as used herein means an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur even under the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind.

Promoter

A sequence of nucleotides from which transcription may be initiated of DNA operably linked downstream (i.e. in the 3' direction on the sense strand of double-stranded DNA). A promoter "drives" transcription of an operably linked sequence. "Operably linked" means joined as part of the same nucleic acid molecule, suitably positioned and oriented for transcription to be initiated from the promoter.

Stringent Hybridization Conditions

"Stringent hybridization conditions" as used herein mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probe molecules complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times stronger than background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

Substantially Complementary

"Substantially complementary" as used herein means that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides, or that the two sequences hybridize under stringent hybridization conditions.

Substantially Identical

"Substantially identical" as used herein means that a first and a second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or with respect to nucleic acids, if the first sequence is substantially complementary to the complement of the second sequence.

Target Nucleic Acid

The target nucleic acid may comprise a target miRNA binding site or a variant thereof. One or more probes may bind the target nucleic acid. The target binding site has a perfect or near-perfect complementarity to one of the miRNA sequences as listed in Sanger database, version 10.1 or the database of Molnar et al, 2007.

Variant

"Variant" as used herein referring to a nucleic acid means (i) a portion of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequence substantially identical thereto.

Wild Type Sequence

As used herein, the term "wild type sequence" refers to a coding, a non-coding or an interface sequence which is an allelic form of sequence that performs the natural or normal function for that sequence. Wild type sequences include multiple allelic forms of a cognate sequence, for example, multiple alleles of a wild type sequence may encode silent or conservative changes to the protein sequence that a coding sequence encodes.

2. Nucleic Acids

"Nucleic acid" or "oligonucleotide" or "polynucleotide", as used herein means at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequences. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated herein by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. $N_6$-methyl adenosine are suitable. The 2'-OH-group may be replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. Modified nucleotides also include nucleotides conjugated with cholesterol through, e.g., a hydroxyprolinol linkage as described in Krutzfeldt et al., Nature 438:685-689 (2005), Soutschek et al., Nature 432:173-178 (2004), and U.S. Patent Publication No. 20050107325, which are incorporated herein by reference. Additional modified nucleotides and nucleic acids are described in U.S. Patent Publication No. 20050182005, which is incorporated herein by reference. Modifications of the ribose-phosphate backbone may be done for a variety of reasons, e.g., to increase the stability and half-life of such molecules in physiological environments, to enhance diffusion across cell membranes, or as probes on a biochip. The backbone modification may also enhance resistance to degradation, such as in the harsh endocytic environment of cells. Mixtures of naturally occurring nucleic acids and analogs may be made; alternatively, mixtures of different nucleic acid analogs, and mixtures of naturally occurring nucleic acids and analogs may be made.

The nucleic acids provided herein comprise the sequences of SEQ ID NOS: 1-88 and variants thereof. The variant may be a complement of the referenced nucleotide sequence. The variant may also be a nucleotide sequence that is substantially identical to the referenced nucleotide sequence or the complement thereof. The variant may also be a nucleotide sequence which hybridizes under stringent conditions to the referenced nucleotide sequence, complements thereof, or nucleotide sequences substantially identical thereto. Accordingly, SEQ ID NOS: 1-88, as well as fragment thereof or sequences at least about 80% identical thereto, or sequences capable of hybridizing to, may be used to modify the oil content in a plant. Cells and transgenic plants produced by transduction of a vector comprising nucleic acids of the invention, are an additional feature of the invention.

The nucleic acid may have a length of from about 10 to about 250 nucleotides. The nucleic acid may have a length of at least 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 125, 150, 175, 200 or 250 nucleotides. The nucleic acid may be synthesized or expressed in a cell (in vitro or in vivo) using a synthetic gene. The nucleic acid may be synthesized as a single strand molecule and hybridized to a substantially complementary nucleic acid to form a duplex. The nucleic acid may be introduced to a cell, tissue or organ in a single- or double-stranded form or capable of being expressed by a synthetic gene using methods well known to those skilled in the art, including as described in U.S. Pat. No. 6,506,559 which is incorporated by reference.

Also contemplated are uses of nucleic acid sequences, also referred to herein as oligonucleotides or polynucleotides, typically having at least 12 bases, preferably at least 15, more preferably at least 20, 30, or 50 bases, which hybridize under at least highly stringent (or ultra-high stringent or ultra-ultra-high stringent conditions) conditions to a polynucleotide sequence described above. Subsequences of the nucleic acid sequences of the invention, including polynucleotide fragments and oligonucleotides are useful as nucleic acid probes and primers. An oligonucleotide suitable for use as a probe or primer is at least about 15 nucleotides in length, more often at least about 18 nucleotides, often at least about 21 nucleotides, frequently at least about 30 nucleotides, or about 40 nucleotides, or more in length. A nucleic acid probe is useful in hybridization protocols, e.g., to identify additional nucleic acid sequences homologs of the invention, including protocols for microarray experiments. Primers can be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods.

2a. MicroRNAs their Processing

MicroRNAs (or miRNAs) are 17 to 24 nucleotide silencing RNAs, processed from a hairpin stem-loop region of a longer transcript precursor, by Dicer-like enzymes.

Plant miRNAs may be found in genomic regions not associated with protein coding genes. Transcription of a gene encoding miRNA genarates a pri-miRNA which is processed by DCL1, optionally with the aid of HYL1 and other factors, to a miRNA:miRNA* duplex which may include 5' phosphates (P) and two-nucleotide 3' overhangs. DCL1 cuts preferentially at specific positions in the miRNA stem-loop precursor. (Pre-miRNAs, which are readily detectable in animals, appear to be short-lived in plants).

The 3' sugars of the miRNA:miRNA* duplex may be methylated possibly within the nucleus. The miRNA is exported to the cytoplasm by HST, probably with the aid of additional factors. The miRNA strand is preferentially loaded into the RNA induced silencing complex (RISC), where it is protected from degradation, whereas the miRNA* strand is preferentially excluded from the silencing complex and consequentially subject to degradation. Accordingly, the final product of the miRNA biogenesis pathway is a single-stranded RNA incorporated into a silencing complex.

Plant miRNAs may facilitate both target cleavage and translational repression. Plant miRNAs may guide the cleavage of complementary or nearly complementary mRNAs, optionally by negatively regulate stability of their targets. Cleavage may occur between the target nucleotides that pair to nucleotides 10 and 11 of the miRNA.

Plant miRNAs may occur in gene families, each family contains several loci within a single genome, each potentially encoding identical or nearly identical mature miRNAs.

The nucleic acids of this invention may comprise a sequence of a miRNA (including miRNA*) or a variant thereof. The miRNA sequence may comprise from 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the precursor. The sequence of the miRNA may also be the last 13-33 nucleotides of the precursor. The sequence of the miRNA may comprise the sequence of SEQ ID NOS: 1-39, 71-73 and 84 or variants thereof. The sequence of the microRNA precursor may comprise the sequence of SEQ ID NOS: 40-70, 74-75 and 85 or variants thereof, as detailed in Table 1.

TABLE 1

Details regarding miRs associated with oil content in *C. reinhardtii* and their corresponding hairpins

| miR SEQ ID NO | Name[1] | Accession | Locus ID | Position in genome | Hairpin SEQ ID NO |
|---|---|---|---|---|---|
| 1 | cre-miR905 | MI00605698 | N/A | scaffold 75: 370850-371142 | 40 |
| 2 | cre-miR908.1 | MI0005701 | N/A | scaffold 213: 20092-20321 | 41 |
| 3 | cre-miR908.2 | MI0005701 | N/A | scaffold 213: 20092-20322 | 41 |
| 4 | cre-miR908.3 | MI0005701 | N/A | scaffold 213: 20092-20323 | 41 |
| 5 | cre-miR910 | MI0005703 | N/A | scaffold 17: 966108-966334 | 42 |
| 6 | cre-miR916 | MI0005711 | N/A | scaffold 86: 94576-95507 | 43 |
| 7 | cre-miR919.1 | MI0005709 | N/A | scaffold 6: 1014120-1014384 | 44 |
| 8 | cre-miR919.2 | MI0005709 | N/A | scaffold 6: 1014120-1014384 | 44 |
| 9 | cre-miR1145.1 | MI0006206 | N/A | scaffold 2: 546495-546515 | 45 |
| 10 | cre-miR1145.2 | MI0006206 | N/A | scaffold2: 546542-546562 | 45 |
| 11 | cre-miR1149.1 | MI0006210 | N/A | scaffold 1: 5256729-5256842 | 46 |
| 12 | cre-miR1149.2 | MI0006210 | N/A | scaffold 1: 5256729-5256842 | 46 |
| 13 | cre-miR1151a | MI0006212 | N/A | scaffold 10: 1934033-1934142 | 47 |
| 14 | cre-miR1151b | MI0006213 | N/A | scaffold 10: 1935781-1935924 | 48 |
| 15 | cre-miR1152 | MI0006214 | N/A | scaffold 12: 1998777-1998906 | 49 |
| 16 | cre-miR1155 | MI0006217 | N/A | scaffold 15: 2058507-2058606 | 50 |
| 17 | cre-miR1157 | MI0006219 | N/A | scaffold 18: 251268-251404 | 51 |
| 18 | cre-miR1160.1 | MI0006221 | N/A | scaffold 26: 727941-728377 | 52 |
| 19 | cre-miR1160.2 | MI0006221 | N/A | scaffold 26: 727941-728377 | 52 |
| 20 | cre-miR1160.3 | MI0006221 | N/A | scaffold 26: 727941-728377 | 52 |

TABLE 1-continued

Details regarding miRs associated with oil content in
C. reinhardtii and their corresponding hairpins

| miR SEQ ID NO | Name[1] | Accession | Locus ID | Position in genome | Hairpin SEQ ID NO |
|---|---|---|---|---|---|
| 21 | cre-miR1167 | MI0006234 | N/A | scaffold 10: 2068926-2069014 | 53 |
| 22 | cre-miR1168.1 | MI0006228 | N/A | scaffold 40: 432487-432679 | 54 |
| 23 | cre-miR1168.2 | MI0006228 | N/A | scaffold 40: 432487-432679 | 54 |
| 24 | cre-miR1169 | MI0006229 | N/A | scaffold 46: 613349-613444 | 55 |
| 25 | cre-miR1171 | MI0006231 | N/A | scaffold 51: 419396-419582 | 56 |
| 26 | CRMIR5 | N/A | cre.02466 | scaffold 35: 929861-929986 | 57 |
| 27 | CRMIR15 | N/A | cre.02674 | scaffold 558: 7360-8065 | 58 |
| 28 | CRMIR16 | N/A | cre.02674 | scaffold 558: 7360-8065 | 59 |
| 29 | CRMIR29 | N/A | cre.02714 | scaffold 6: 118475-118760 | 60 |
| 30 | CRMIR47 | N/A | cre.01795 | scaffold 1: 186381-186552 | 61 |
| 31 | CRMIR72 | N/A | cre.01824 | scaffold 1: 6352149-6352516 | 62 |
| 32 | CRMIR96 | N/A | cre.01854 | scaffold 10: 2282657-2282780 | 63 |
| 33 | CRMIR100 | N/A | cre.02194 | scaffold 2: 3204761-3204858 | 64 |
| 34 | CRMIR101 | N/A | cre.02194 | scaffold 2: 3204761-3204858 | 65 |
| 35 | CRMIR121 | N/A | cre.02790 | scaffold 68: 317493-317595 | 66 |
| 36 | CRMIR123 | N/A | cre.02790 | scaffold 68: 317605 . . . 317763 | 67 |
| 37 | CRMIR129 | N/A | cre.02862 | scaffold 75: 284481-284798 | 68 |
| 38 | CRMIR152 | N/A | cre.03680 | TIN168528_x1: 64 . . . 367 | 69 |
| 39 | CRMIR156 | N/A | cre.04503 | TIN455283_x1: 587 . . . 648 | 70 |
| 71 | cre-miR1142 | MI0006203 | NA | scaffold 34: 1054527-1055286 | 74 |
| 72 | CRMIR136 | N/A | 02884 | scaffold 80: 14307-15220 | 75 |
| 73 | CRMIR137 | N/A | 02884 | scaffold 80: 14307-15220 | 75 |
| 84 | CRMIR167 | N/A | cre.05507 | scaffold 17: 1800973-1801124 | 85 |

[1]The miRs of SEQ ID NOS: 1-25, 71 and their corresponding hairpins (SEQ ID NOS: 40-56, 74) appear in the Sanger database, version 10.1. Sequences 26-39, 72-73, 84 and their corresponding hairpins (SEQ ID NOS: 57-70, 75, 85) are in accordance with the database of Molnar et al, 2007.

3. Transgenic Plants

A transgenic plant as used herein refers to a plant that contains genetic material not found in a wild-type plant of the same species, variety or cultivar. The genetic material may include a transgene, an insertional mutagenesis event (such as by transposon or T-DNA insertional mutagenesis), an activation tagging sequence, a mutated sequence, a homologous recombination event or a sequence modified by chimeraplasty. Typically, the foreign genetic material has been introduced into the plant by human manipulation, but any method can be used as one of skill in the art recognizes. A transgenic plant may contain an expression vector or cassette.

Successful examples of the modification of plant characteristics by transformation with cloned sequences which serve to illustrate the current knowledge in this field of technology, and which are herein incorporated by reference, include U.S. Pat. Nos. 6,235,529, 7,429,691 and 7,256,283.

The particular choice of a transformation technology will be determined by its efficiency to transform certain plant species as well as the experience and preference of the person practicing the invention with a particular methodology of choice. It will be apparent to the skilled person that the particular choice of a transformation system to introduce nucleic acid into plant cells is not essential to or a limitation of the invention, nor is the choice of technique for plant growth.

Following transformation, plants are preferably selected using a dominant selectable marker incorporated into the transformation vector. Typically, such a marker will confer antibiotic or herbicide resistance on the transformed plants and selection of transformants can be accomplished by exposing the plants to appropriate concentrations of the antibiotic or herbicide.

After transformed plants are selected and grown to maturity, those plants showing a modified trait are identified. The modified trait can be enhanced oil content.

Additionally, to confirm that the modified trait is due to changes in expression levels or activity of nucleic acid sequences of the invention, mRNA expression can be analyzed by using Northern blots, RT-PCR or microarrays.

3.1 Transgenic miR-Based Enhancement of Oil Yield in Plants' Seeds

In order to enhance the oil content in plants' seeds according to some aspects of the invention, various varieties of plants differing in oil content, of Canola, soybean, Jatropha, camelina, corn and castor bean (widely used for biodiesel production) are obtained, and throughout their various developmental stages, including floral tissue and young seeds, RNA is extracted and microRNA expression profiles are created and compared.

For example, two corn varieties, named sweet and super-sweet (both obtained from Galil Seeds—Israel), have oil contents of 7% and 18% respectively. RNA is extracted from four days old seedlings of these two varieties, and microarray analysis is performed by LC Sciences (Austin, Tex.). The microRNA expression profiles of these varieties are compared.

Differentially expressed microRNAs related to seed oil content are identified and validated by qPCR. Plants are transgenically transformed to overexpress microRNA precursors or to express microRNA-resistant targets. Transgenic plants are grown parallel to corresponding wild-type plants, and genetically transformed plants with relatively enhanced seed oil content are identified.

3.2 Algal Technology

Although there are thousands of species of known naturally occurring algae, any one may be used for biodiesel production according to some embodiments of the invention. The skilled artisan will realize that different algal strains will exhibit different growth and oil productivity and that under different conditions the system may contain a single strain of algae or a mixture of strains with different properties, or strains of algae plus symbotic bacteria. The algal species used may be optimized for geographic location, temperature sensitivity, light intensity, pH sensitivity, salinity, water quality, nutrient availability, seasonal differences in temperature or light, the desired end products to be obtained from the algae and a variety of other factors.

3.3 Genetic Modification of Algae

The genetic modification of algae for specific product outputs is relatively straight forward using techniques well known in the art. In certain embodiments, algae of use to produce biodiesel may be genetically engineered (transgenic) to contain one or more isolated nucleic acid sequences that enhance oil production or provide other characteristics of use for algal culture, growth, harvesting or use. Methods of stably transforming algal species and compositions comprising isolated nucleic acids of use are well known in the art and any such methods and compositions may be used in the practice of the present invention. Exemplary transformation methods of use may include microprojectile bombardment, electroporation, protoplast fusion, PEG-mediated transformation, DNA-coated silicon carbide whiskers or use of viral mediated transformation (see, e.g., Sanford et al., 1993, Meth. Enzymol. 217:483-509; Dunahay et al., 1997, Meth. Molec. Biol. 62:503-9, incorporated herein by reference).

U.S. Pat. No. 5,661,017 discloses methods for algal transformation of chlorophyll C-containing algae, such as the Bacillariophyceae, Chrysophyceae, Phaeophyceae, Xanthophyceae, Raphidophyceae, Prymnesiophyceae, Cryptophyceae, Cyclotella, Navicula, Cylindrotheca, Phaeodactylum, Amphora, Chaetoceros, Nitzschia or Thalassiosira.

Following transformation, algae are preferably selected using a dominant selectable marker incorporated into the transformation vector. Typically, such a marker will confer antibiotic or other resistance on the transformed algae and selection of transformants can be accomplished by exposing the algae to appropriate concentrations of the selectable marker to select for transformed algae. Selectable markers of use may include, neomycin phosphotransferase, aminoglycoside phosphotransferase, aminoglycoside acetyltransferase, aminoglycoside-O-phosphotransferase, chloramphenicol acetyl transferase, hygromycin B phosphotransferase, bleomycin binding protein, phosphinothricin acetyltransferase, bromoxynil nitrilase, glyphosate-resistant 5-enolpyruvylshikimate-3-phosphate synthase, cryptopleurine-resistant ribosomal protein S 14, emetine-resistant ribosomal protein S 14, sulfonylurea-resistant acetolactate synthase, imidazolinane-resistant acetolactate synthase, streptomycin-resistant 16S ribosomal RNA, spectinomycin-resistant 16S ribosomal RNA, erythromycin-resistant 23 S ribosomal RNA or methyl benzimidazole-resistant tubulin. Regulatory nucleic acid sequences to enhance expression of a transgene are known, such as *C. cryptica* acetyl-CoA carboxylase 5'-untranslated regulatory control sequence, a *C. cryptica* acetyl-CoA carboxylase 3'-untranslated regulatory control sequence, and combinations thereof.

Additional possible selection is via auxotroph mutants. The selectable marker is then a biosynthetic gene allowing the mutant to grow in the absence of the substance they are auxotroph to. This includes the ability to synthesize amino acids, vitamins and other essential co-factors. A specific example is the ARG7 locus that can rescue the arg2 mutation in *C. reinhardtii* (Debuchy et al. (1989) EMBO J. 8, 2803-2809) and allow cells to grow in the absence of the amino acid arginine.

3.4 Separation of Algae and Extraction of Oil

In various embodiments, algae may be separated from the medium, and various algal components, such as oil, may be extracted using any method known in the art. For example, algae may be partially separated from the medium using a standing whirlpool circulation, harvesting vortex and/or sipper tubes, as discussed below. Alternatively, industrial scale commercial centrifuges of large volume capacity may be used to supplement or in place of other separation methods. Such centrifuges may be obtained from known commercial sources (e.g., Cimbria Sket or IBG Monforts, Germany; Alfa Laval AJS, Denmark). Centrifugation, sedimentation and/or filtering may also be of use to purify oil from other algal components. Separation of algae from the aqueous medium may be facilitated by addition of flocculants, such as clay (e.g., particle size less than 2 microns), aluminum sulfate or polyacrylamide. In the presence of flocculants, algae may be separated by simple gravitational settling, or may be more easily separated by centrifugation.

The skilled artisan will realize that any method known in the art for separating cells, such as algae, from liquid medium may be utilized. For example, U.S. Pat. No. 6,524,486, incorporated herein by reference, discloses a tangential flow filter device and apparatus for partially separating algae from an aqueous medium. Other published methods for algal separation and/or extraction may also be used. (See, e.g., Rose et al., Water Science and Technology 1992, 25:319-327; Smith et al., Northwest Science, 1968, 42:165-171; Moulton et al., Hydrobiologia 1990, 204/205:401-408; Borowitzka et al., Bulletin of Marine Science, 1990, 47:244-252; Honeycutt, Biotechnology and Bioengineering Symp. 1983, 13:567-575).

In various embodiments, algae maybe disrupted to facilitate separation of oil and other components. Any method known for cell disruption may be utilized, such as ultrasonication, French press, osmotic shock, mechanical shear force, cold press, thermal shock, rotor-stator disruptors, valve-type processors, fixed geometry processors, nitrogen decompression or any other known method. High capacity commercial cell disruptors may be purchased from known sources. (E.g., GEA Niro Inc., Columbia, Md.; Constant Systems Ltd., Daventry, England; Microfluidics, Newton, Mass.).

4. Promoters

Promoters are expressed in many, if not all, cell types of many plants. Promoters including those that are developmentally regulated or inducible may be used. For example, if it is necessary to silence the target gene specifically in a particular cell type the construct may be assembled with a promoter that drives transcription only in that cell type. Similarly, if the target gene is to be silenced following a defined external stimulus the construct may incorporate a promoter that is be activated specifically by that stimulus. Promoters that are both tissue specific and inducible by specific stimuli may be used.

A variety of plant gene promoters that regulate gene expression in response to environmental, hormonal, chemical, developmental signals, and in a tissue-active manner can be used in plants. Choice of a promoter is based largely on the phenotype of interest and is determined by such factors as tissue (e.g., seed, fruit, root, pollen, vascular tissue, flower, carpel, etc.), inducibility (e.g., in response to wounding, heat, cold, drought, light, pathogens, etc.), timing, developmental stage, and the like. Numerous known promoters have been characterized and can favorably be employed to promote expression of a polynucleotide of the invention in a transgenic plant or cell of interest.

5. Biochip

A biochip is also provided. The biochip may comprise a solid substrate comprising an attached probe or plurality of probes described herein. The probes may be capable of hybridizing to a target sequence under stringent hybridization conditions. The probes may be attached at spatially defined addresses on the substrate. More than one probe per target sequence may be used, with either overlapping probes or probes to different sections of a particular target sequence. The probes may either be synthesized first, with subsequent attachment to the biochip, or may be directly synthesized on the biochip.

The solid substrate may be a material that may be modified to contain discrete individual sites appropriate for the attachment or association of the probes and is amenable to at least one detection method. Representative examples of substrates include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate may be planar, although other configurations of substrates may be used as well. For example, probes may be placed on the inside surface of a tube, for flow-through sample analysis to minimize sample volume. Similarly, the substrate may be flexible, such as flexible foam, including closed cell foams made of particular plastics.

The biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linker. The probes may be attached to the solid support by either the 5' terminus, 3' terminus, or via an internal nucleotide.

The probe may also be attached to the solid support non-covalently. For example, biotinylated oligonucleotides can be made, which may bind to surfaces covalently coated with streptavidin, resulting in attachment. Alternatively, probes may be synthesized on the surface using techniques such as photopolymerization and photolithography.

6. Expression Vector

The expression vector or cassette typically comprises an encoding sequence operably linked (i.e., under regulatory control of) to appropriate inducible or constitutive regulatory sequences that allow for the expression of polypeptide. The expression vector can be introduced into a plant by transformation or by breeding after transformation of a parent plant. A plant refers to a whole plant as well as to a plant part, such as seed, fruit, leaf, or root, plant tissue, plant cells or any other plant material, e.g., a plant explant, as well as to progeny thereof, and to in vitro systems that mimic biochemical or cellular components or processes in a cell.

A number of expression vectors suitable for stable transformation of plant cells or for the establishment of transgenic plants have been described including those described in Weissbach and Weissbach (1989) Methods for Plant Molecular Biology, Academic Press, and Gelvin et al. (1990) Plant Molecular Biology Manual, Kluwer Academic Publishers. Specific examples include those derived from a Ti plasmid of *Agrobacterium tumefaciens*, as well as those disclosed by Herrera-Estrella et al. (1983) Nature 303: 209, Bevan (1984) Nucleic Acids Res. 12: 8711-8721, Klee (1985) Bio/Technology 3: 637-642, for dicotyledonous plants.

Alternatively, non-Ti vectors can be used to transfer the DNA into monocotyledonous plants and cells by using free DNA delivery techniques. Such methods can involve, for example, the use of liposomes, electroporation, microprojectile bombardment, silicon carbide whiskers, and viruses. By using these methods transgenic plants such as wheat, rice (Christou (1991) Bio/Technology 9: 957-962) and corn (Gordon-Kamm (1990) Plant Cell 2: 603-618) can be produced. An immature embryo can also be a good target tissue for monocots for direct DNA delivery techniques by using the particle gun (Weeks et al. (1993) Plant Physiol. 102: 1077-1084; Vasil (1993) Bio/Technology 10: 667-674; Wan and Lemeaux (1994) Plant Physiol. 104: 37-48, and for Agrobacterium-mediated DNA transfer (Ishida et al. (1996) Nature Biotechnol. 14: 745-750).

Typically, plant transformation vectors include one or more cloned plant coding sequence (genomic or cDNA) under the transcriptional control of 5' and 3' regulatory sequences and a dominant selectable marker. Such plant transformation vectors typically also contain a promoter, a transcription initiation start site, an RNA processing signal (such as intron splice sites), a transcription termination site, and/or a polyadenylation signal.

EXAMPLES

Example 1

Materials and Methods a. Algal material: The *Chlamydomonas reinhardtii* UTEX 90 strain (University of Texas algae collection, Austin Tex.) was used in all experiments except for transformation experiments where the cell wall-less mutant cw15 (Chlamydomonas Center, Duke University) was used.

Algae were maintained in TAP medium in an Adaptis growth chamber (Conviron, Canada) at 22° C. under constant white light at an intensity of 175 μmol photon m$^{-2}$ s$^{-1}$ while being shaken at 120 rpm in 250-ml flasks containing 50 ml of growth medium.

Nitrogen starvation experiments were performed using either Bristol medium (NaNO$_3$-2.94 mM, CaCl$_2$.2H$_2$O-0.17 mM, MgSO$_4$.7H$_2$O-0.3 mM, K$_2$HPO$_4$-0.43 mM, KH$_2$PO$_4$-1.29 mM, NaCl-0.43 mM) or Bristol medium depleted of NaNO$_3$, for nitrate-limiting conditions.

b. Database: MicroRNA sequences were derived from the 10.1 version of miRBase released December 2007 and consists of the 673 non-redundant sequences defined as "Viridiplantae" and the 47 sequences submitted for *C. reinhardtii*. Additionally, 170 recently-identified putative microRNA sequences by present in the *C. reinhardtii* silencing RNA database were included.

c. Microarray design: Custom microarrays were manufactured by Agilent Technologies by in situ synthesizing DNA oligonucleotide probes for 890 plant and algal microRNAs with each probe being printed in triplicate.

Fourteen negative control probes were designed using the sense sequences of different microRNAs, chosen from different plants and algae. Two groups of positive control probes were used: (i) synthetic small RNA that were spiked to the RNA before labeling to verify the labeling efficiency, and (ii) probes for abundant small nuclear RNAs (U1, U2, U3, U4, U5, U6, for three plant species and for *C. reinhardtii*) were spotted on the array to verify RNA's quantity and quality.

d. Sample labeling: Five μg of total RNA were labeled by ligation of an RNA-linker, p-rCrU-Cy/dye (Eurogentec), to the 3'-end with Cy3 or Cy5. The labeling reaction contained total RNA, spikes (0.1-20 fmoles), 300-400 ng RNA-linker-dye, 15% DMSO, 1× ligase buffer and 20 units of T4 RNA ligase (NEB) and proceeded at 4° C. for 1hr followed by 1 hr at 37° C. on PCR machine.

e. Microarray hybridization and scanning: Five micrograms of total RNA were labeled by ligation of Cy3 or Cy5 to the 3'-end. The labeled RNA was mixed with 3× hybridization buffer (Ambion, Austin Tex.) and hybridized with the slides for 12-16 hrs in an Agilent Rotational oven at 10-13 rpm. Following the hybridization, the arrays were washed twice in room temperature with 1×SSC and 0.2% SDS. Next, the arrays were washed in 0.1×SSC followed by a 1 min wash in fresh Agilent Stabilization and Drying solution (Agilent, Santa Clara Calif.).

f. Array signal calculation and normalization: Array images were analyzed using the Feature Extraction software (FE) 9.5.1 (Agilent, Santa Clara Calif.). Experiments were repeated four times and triplicate spots were combined to produce one signal for each probe by taking the logarithmic mean of reliable spots. All data was log-transformed (natural base) and the analysis was performed in log-space. A reference data vector for normalization R was calculated by taking the median expression level for each probe across nitrogen starvation samples. For each sample data vector S, a 2nd degree polynomial F was found so as to provide the best fit between the sample data and the reference data, such that R=F(S). For each probe in the sample (element $S_i$ in the vector S), the normalized value (in log-space) $M_i$ was calculated from the initial value $S_i$ by transforming it with the polynomial function F, so that $M_i$=F($S_i$). P-values were calculated using a two-sided t-test on the log-transformed normalized fluorescence signal. For each microRNA the fold-difference (ratio of the median normalized fluorescence) was calculated.

Example 2

Oil Biosynthesis Induced by Nitrogen Starvation and Strong Light, and Differentially Expressed MicroRNAs Related Thereto 2.1 Induction of Oil Biosynthesis in *C. Reinhardtii*

The oil content in *C. reinhardtii* was monitored under two different sets of conditions: nitrogen starvation and strong light.

Nitrogen starvation: *C. reinhardtii* cells were grown to logarithmic phase in algae culture broth and 50-ml aliquots were collected by centrifugation at 3,220×g for 1 minute. Cells were washed once in 25 ml of either Bristol (for nitrogen sufficient conditions) or Bristol medium without NaNO$_3$ (Bristol-N$_2$) (for nitrogen limiting conditions) and resuspended in 50 ml of either Bristol or Bristol-N$_2$ medium respectively. Cells were shaken at 120 rpm at 22° C. under constant light and were harvested after 24 hrs.

Light induction: *C. reinhardtii* cells were grown to logarithmic phase under standard light conditions (1×18 Watts white fluorescent lamp). For oil induction the standard light was supplemented with 4×36 Watts lamps.

Cells were harvested after 6, 16, 24 and 48 hours, and the oil content of control and treated cells was performed using Nile Red staining and measuring the fluorescence. 200 μl of algal cells were placed in a 96-well plate (Costar 3596), mixed with 10 μl of Nile Red solution (N3013, Sigma. 1 mg/ml stock in 2-propanol) and incubated for 15 minutes at room-temperature. Fluorescence was measured using a Thermo Electron Fluroskan Ascent with excitation at 544 nm and emission at 590 nm. 200 μl of fresh growth media with 20 μl of Nile Red were used for blank measurements. Fluorescence was normalized against cell density as measured by an ELx808 microplate reader (BIOTEK Instruments Inc.) at 450 nm.

As indicated in FIG. 1, the kinetics of oil content induction was found to be different for nitrogen starvation and strong light. Nitrogen starvation caused a noticeable induction already after 16 hours with a peak at 24 hours, whereas induction by strong light was only noticed after 24 hours but seems to grow stronger over time at least until 48 hours.

2.2 Differentially Expressed MicroRNAs

Nitrogen starvation experiments were performed by growing *C. reinhardtii* to logarithmic phase, washing off traces of nitrogen from the growth medium and divided into two treatments containing Bristol medium with or without NaNO$_3$ as a nitrogen source. Cells were grown for 16, 24 and 48 hours after which RNA was extracted and used for microRNA array analysis. Similarly, RNA was extracted from *C. reinhardtii* cells that were grown to logarithmic phase under standard light or strong light. The RNA was extracted after 6, 16 or 24 hours and was used for microRNA array analysis.

Total RNA was extracted using the mirVana™ kit (Ambion, Austin Tex.) following the instruction manual for total RNA isolation protocol using the following adaptations: 50 ml of alga cells were harvested by centrifugation at 4,000 rpm for 1 minute, washed once with 25 ml of cold algae culture broth medium and re-suspended in 2 ml of the mirVana™ kit Lysis/Binding Buffer. Cells were ground using a Polytron PT-MR 2100 homogenizer (Kinematica A G, Switzerland).

Expression levels of microRNAs in each of the treatments were measured as described in Materials and Methods section.

MicroRNAs upregulated and downregulated in *C. reinhardtii* under nitrogen starvation are shown in Tables 2a and 2b respectively. MicroRNAs upregulated and downregulated in response to strong light are shown in Tables 3a and 3b respectively.

TABLE 2: MicroRNAs up-regulated (a) and down-regulated (b) in response to nitrogen starvation (Bristol-$N_2$).

Only microRNAs demonstrating a minimum fold change of 1.5 in (a) or 0.6 in (b) in at least one of the time points are shown. Normalized expression values are shown in log scale.

TABLE 2a

MicroRNAs upregulated in response to nitrogen starvation.

| MicroRNA | SEQ ID NO | 16 hours: $-N_2$ | $+N_2$ | Fold Change | 24 hours: $-N_2$ | $+N_2$ | Fold Change | 48 hours: $-N_2$ | $+N_2$ | Fold Change |
|---|---|---|---|---|---|---|---|---|---|---|
| CRMIR29 | 29 | 8.1 | 7.7 | 1.4 | 8.5 | 7.8 | 1.6 | 8.1 | 8.1 | 1.0 |
| CRMIR47 | 30 | 12.0 | 12.1 | 1.0 | 12.3 | 12.3 | 1.0 | 12.7 | 12.1 | 1.5 |
| cre-miR908.3 | 4 | 8.4 | 8.5 | 1.0 | 8.3 | 8.3 | 1.0 | 8.8 | 8.0 | 1.8 |
| cre-miR916 | 6 | 12.8 | 12.4 | 1.4 | 10.1 | 9.4 | 1.7 | 12.2 | 11.9 | 1.3 |
| cre-miR1149.2 | 12 | 7.3 | 7.1 | 1.1 | 7.8 | 7.1 | 1.5 | 7.8 | 7.7 | 1.0 |
| cre-miR1160.3 | 20 | 8.5 | 8.6 | 0.9 | 8.1 | 7.8 | 1.3 | 8.6 | 8.0 | 1.5 |
| cre-miR1171 | 25 | 10.0 | 9.9 | 1.1 | 9.4 | 9.5 | 1.0 | 10.1 | 9.5 | 1.5 |

TABLE 2b

MicroRNAs downregulated in response to nitrogen starvation.

| MicroRNA | SEQ ID NO | 16 hours: $-N_2$ | $+N_2$ | Fold Change | 24 hours: $-N_2$ | $+N_2$ | Fold Change | 48 hours: $-N_2$ | $+N_2$ | Fold Change |
|---|---|---|---|---|---|---|---|---|---|---|
| CRMIR15 | 27 | 8.2 | 8.2 | 1.0 | 5.6 | 5.6 | 1.0 | 6.4 | 7.5 | 0.5 |
| CRMIR16 | 28 | 7.6 | 7.7 | 1.0 | 5.6 | 5.6 | 1.0 | 5.9 | 7.1 | 0.4 |
| CRMIR96 | 32 | 10.8 | 10.8 | 1.0 | 10.7 | 10.9 | 0.9 | 10.4 | 11.0 | 0.7 |
| CRMIR129 | 37 | 10.4 | 10.4 | 1.0 | 9.5 | 10.2 | 0.6 | 10.1 | 10.2 | 0.9 |
| CRMIR152 | 38 | 8.4 | 8.5 | 0.9 | 5.6 | 5.6 | 1.0 | 6.8 | 7.8 | 0.5 |
| cre-miR910 | 5 | 9.6 | 9.9 | 0.9 | 9.9 | 10.4 | 0.7 | 10.7 | 11.7 | 0.5 |
| cre-miR1155 | 16 | 13.3 | 13.1 | 1.1 | 12.2 | 12.9 | 0.6 | 12.9 | 13.0 | 0.9 |
| cre-miR1157 | 17 | 11.5 | 11.5 | 0.9 | 11.9 | 12.5 | 0.7 | 11.9 | 11.7 | 1.1 |
| cre-miR1168.2 | 23 | 11.6 | 11.8 | 0.9 | 10.3 | 10.9 | 0.6 | 11.2 | 11.3 | 1.0 |

Table 3: MicroRNAs upregulated (a) and down-regulated (b) in response to strong light. Normalized expression values are shown in log scale.

TABLE 3a

MicroRNAs up-regulated in response to strong light.

| MicroRNA | SEQ ID NO: | Standard light | Strong light 6 hours | Fold change | 16 hours | Fold change | 24 hours | Fold change |
|---|---|---|---|---|---|---|---|---|
| CRMIR5 | 26 | 12.30 | 13.05 | 1.62 | 13.40 | 2.00 | 12.30 | 1.07 |
| CRMIR72 | 31 | 11.59 | 12.10 | 1.42 | 12.17 | 1.49 | 12.12 | 1.44 |
| CRMIR101 | 34 | 9.18 | 9.88 | 1.62 | 10.38 | 2.29 | 10.05 | 1.82 |
| CRMIR121 | 35 | 6.94 | 7.54 | 1.52 | 7.66 | 1.65 | 7.36 | 1.34 |
| cre-miR919.2 | 8 | 11.80 | 12.59 | 1.72 | 12.34 | 1.45 | 12.96 | 2.23 |
| cre-miR1151a | 13 | 12.83 | 13.69 | 1.82 | 13.81 | 1.97 | 13.84 | 2.01 |
| cre-miR1151b | 14 | 12.84 | 13.78 | 1.92 | 13.73 | 1.85 | 13.83 | 1.99 |
| cre-miR1152 | 15 | 11.61 | 12.86 | 2.39 | 12.25 | 1.56 | 12.12 | 1.43 |
| cre-1167 | 21 | 9.73 | ND | ND | 11.04 | 1.3 | ND | ND |
| cre-miR1169 | 24 | 10.51 | 11.20 | 1.61 | 11.43 | 1.90 | 11.53 | 2.03 |
| CRMIR167 | 84 | 10.2 | 10.4 | 1.26 | 11.1 | 1.8 | 11.0 | 1.6 |

ND: Not Detected

TABLE 3b

MicroRNAs and downregulated in response to strong light.

| MicroRNA | SEQ ID NO: | Standard light | Strong light | | | | |
|---|---|---|---|---|---|---|---|
| | | | 6 hours | Fold change | 16 hours | Fold change | 24 hours | Fold change |

| MicroRNA | SEQ ID NO: | Standard light | 6 hours | Fold change | 16 hours | Fold change | 24 hours | Fold change |
|---|---|---|---|---|---|---|---|---|
| CRMIR15 | 27 | 9.69 | 6.95 | 0.15 | 6.53 | 0.11 | 6.20 | 0.09 |
| CRMIR16 | 28 | 9.00 | 6.57 | 0.19 | 6.33 | 0.16 | 6.06 | 0.13 |
| CRMIR152 | 38 | 10.19 | 7.12 | 0.12 | 6.98 | 0.11 | 6.62 | 0.08 |
| CRMIR156 | 39 | 7.82 | 6.87 | 0.52 | 7.00 | 0.57 | 6.83 | 0.50 |
| cre-miR905 | 1 | 9.40 | 8.54 | 0.55 | 8.59 | 0.57 | 8.13 | 0.41 |
| cre-miR1145.1 | 9 | 7.93 | 7.25 | 0.62 | 7.10 | 0.56 | 6.85 | 0.47 |

Example 3

Oil Biosynthesis Related to Nitrate-Limiting Conditions, and Differentially Expressed MicroRNAs Related Thereto 3.1 Induction of Oil Biosynthesis in *C. Reinhardtii*

*C. reinhardtii* cells were grown to logarithmic phase in TAP medium and 50 ml aliquots were collected by centrifugation at 3,220×g for 1 minute. Cells were washed once in 25 ml of either Bristol medium (nitrate-sufficient conditions) or nitrate-free Bristol medium (nitrate-limiting conditions) and resuspended in 50 ml of either Bristol or nitrate-free Bristol medium respectively. Cells were shaken at 120 rpm at 22° C. and were harvested after 24 hrs.

Relative evaluation of neutral lipids content was performed using Nile Red staining, with some minor modifications: 200 µl of algal cells were placed in a 96-well plate (Costar 3596), mixed with 10 µl of Nile Red solution (N3013, Sigma. 1 mg/ml stock in acetone) and incubated for 10 minutes at room-temperature. Fluorescence was measured using a Thermo Electron Fluroskan Ascent with excitation at 485 nm and emission at 590 nm, which were previously found to detect mainly neutral lipids. 200 µl of fresh growth media with 10 µl of Nile Red were used for blank measurements. Fluorescence was normalized against cell density as measured by an ELx808 microplate reader (BIOTEK Instruments Inc) at 630 nm and verified by cell count of selected samples. The significance of the change in lipid content was calculated by using one sided student's t-test. The relative changes in lipid content between different samples were verified by the gravimetric method, performed by the Mylnefield Lipid Analysis laboratory (Dundee, Scotland).

Neutral lipid content was found to increase in nitrate-limiting conditions by 33% as measured by nile-red staining (p value=0.02) and by 24% by the gravimetric method.

3.2 Differentially Expressed MicroRNAs

Total RNA was extracted using the mirVana™ kit (Ambion, Austin Tex.) following the instruction manual. Samples were DNAse-treated (Ambion, Austin Tex.) for 2 hours, phenol-treated and ethanol-precipitated. Total RNA concentration was determined using an ND-1000 NanoDrop spectrophotometer (Thermo Scientific, Waltham Mass.).

Expression levels of microRNAs in *C. reinhardtii* cells grown under nitrate-sufficient or nitrate-limiting conditions were measured as described in example 2. Comparing the expression levels, five microRNAs were identified that were differentially expressed in these conditions, with a p value≤0.05 and a minimum fold change of 1.5. As detailed in table 4 below, all of the differentially-expressed microRNAs were found to be downregulated in nitrate-limiting relative to nitrate-sufficient conditions.

TABLE 4

Differentially expressed microRNAs in nitrate-sufficient relative to nitrate-limiting conditions

| MicroRNA name | SEQ ID NO: | Fold change | p value |
|---|---|---|---|
| cre-miR1142 | 71 | 1.6 | 0.04 |
| cre-miR1167 | 21 | 1.6 | 0.03 |
| CRMIR129 | 37 | 1.5 | 0.02 |
| CRMIR136 | 72 | 1.5 | 0.02 |
| CRMIR137 | 73 | 1.9 | 0.02 |

Figure 3:
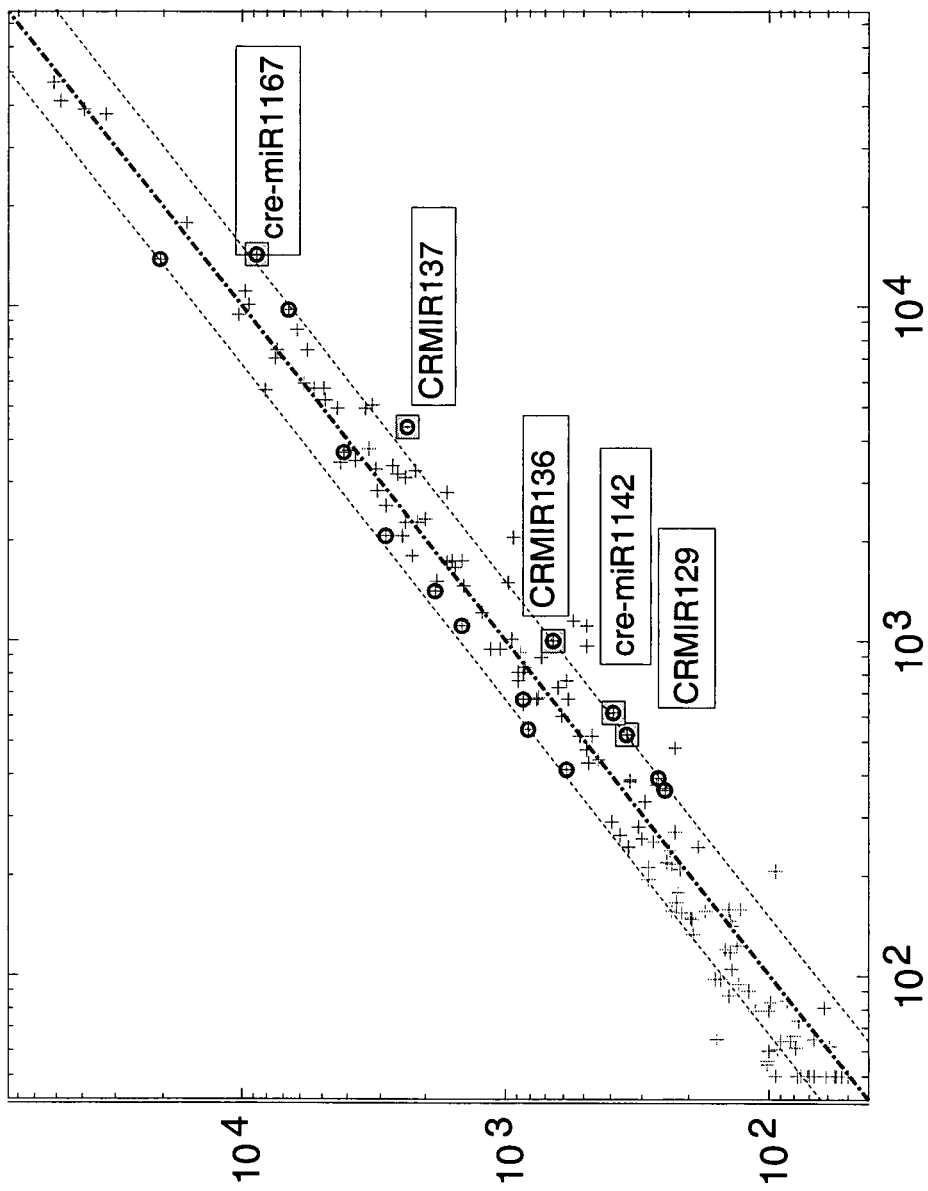
FIG. 3 shows the microRNA array results in response to growth of *C. reinhardtii* in nitrate-limiting conditions (Bristol medium without NaNO$_3$) or nitrate-sufficient conditions (standard Bristol medium). The Y-axis shows the mean normalized expression level of four experiments conducted in nitrate-limiting conditions, and the X-axis shows the mean normalized expression level of four controls grown in nitrate-sufficient conditions. The middle diagonal line represents the expected expression for non-differentially expressed miRNAs (same expression level in nitrate-sufficient and nitrate-limiting conditions) and the other diagonal lines represent fold 1.5 factor lines. Significantly differentially expressed miRs include cre-miR1142 (SEQ ID NO: 71), cre-miR1167 (SEQ ID NO: 21), CRM1R129, (SEQ ID NO: 37), CRMIR136 (SEQ ID NO: 72) and CRMIR137 (SEQ ID NO: 73). All of the significantly differentially expressed miRs were found to be downregulated in response to nitrate-limiting conditions.
Figure 4A:
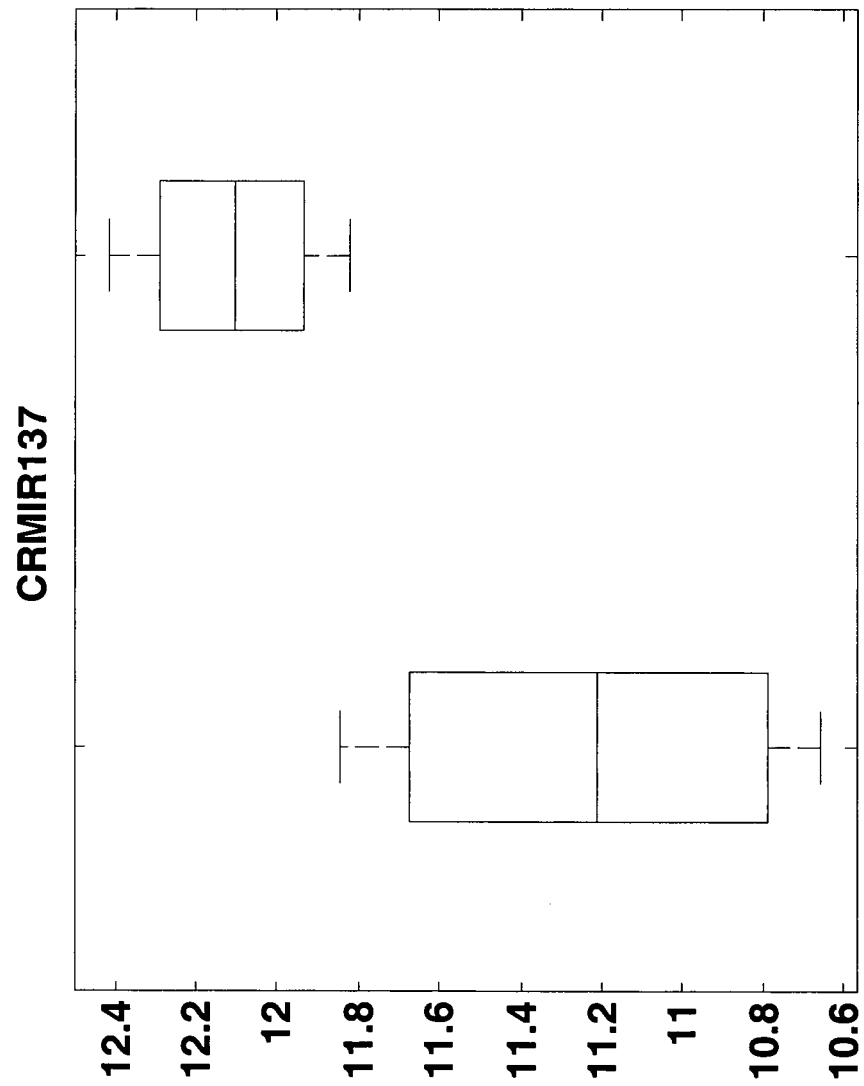
FIGS. 4A-4E are boxplot presentations comparing distributions of the expression values (Y axis) of miRs with differential expression in nitrate-limiting conditions (the left box) vs. nitrate-sufficient conditions (the right box). The line in the box indicates the median expression value, the box top and bottom boundaries indicate the 75th and 25th percentiles respectively, and the horizontal lines and crosses (outliers) show the full range of signals in each group.
Figure 4B:
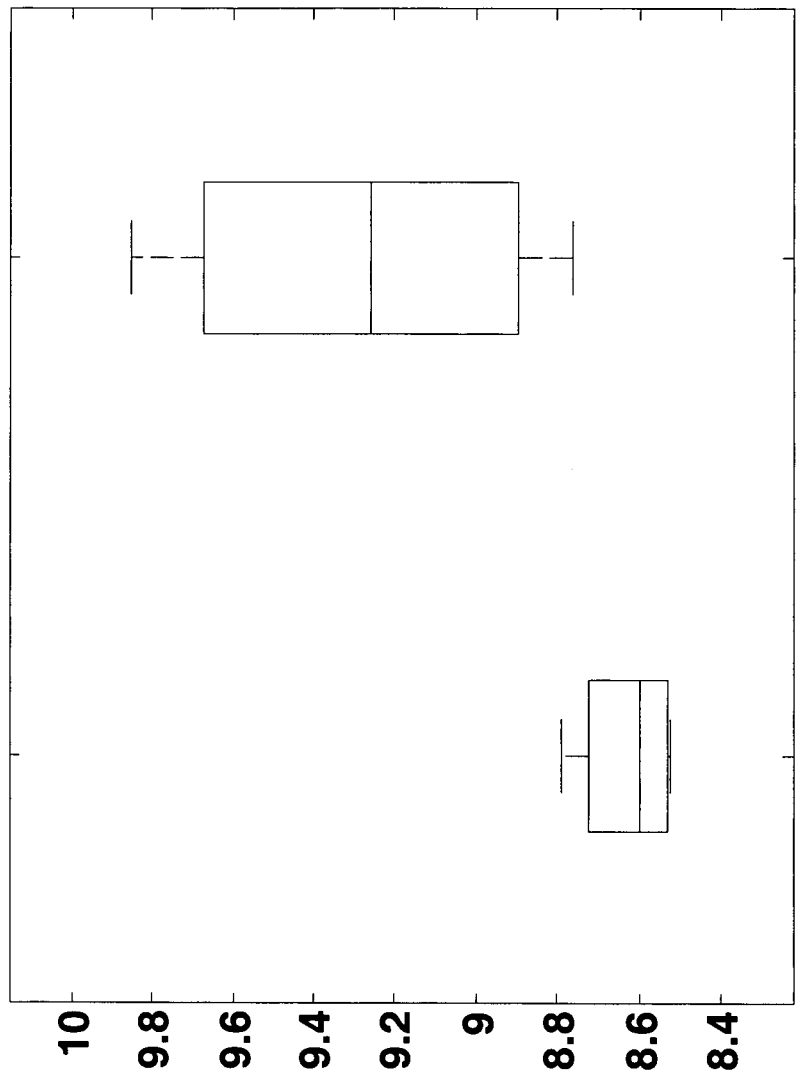
Figure 4C:
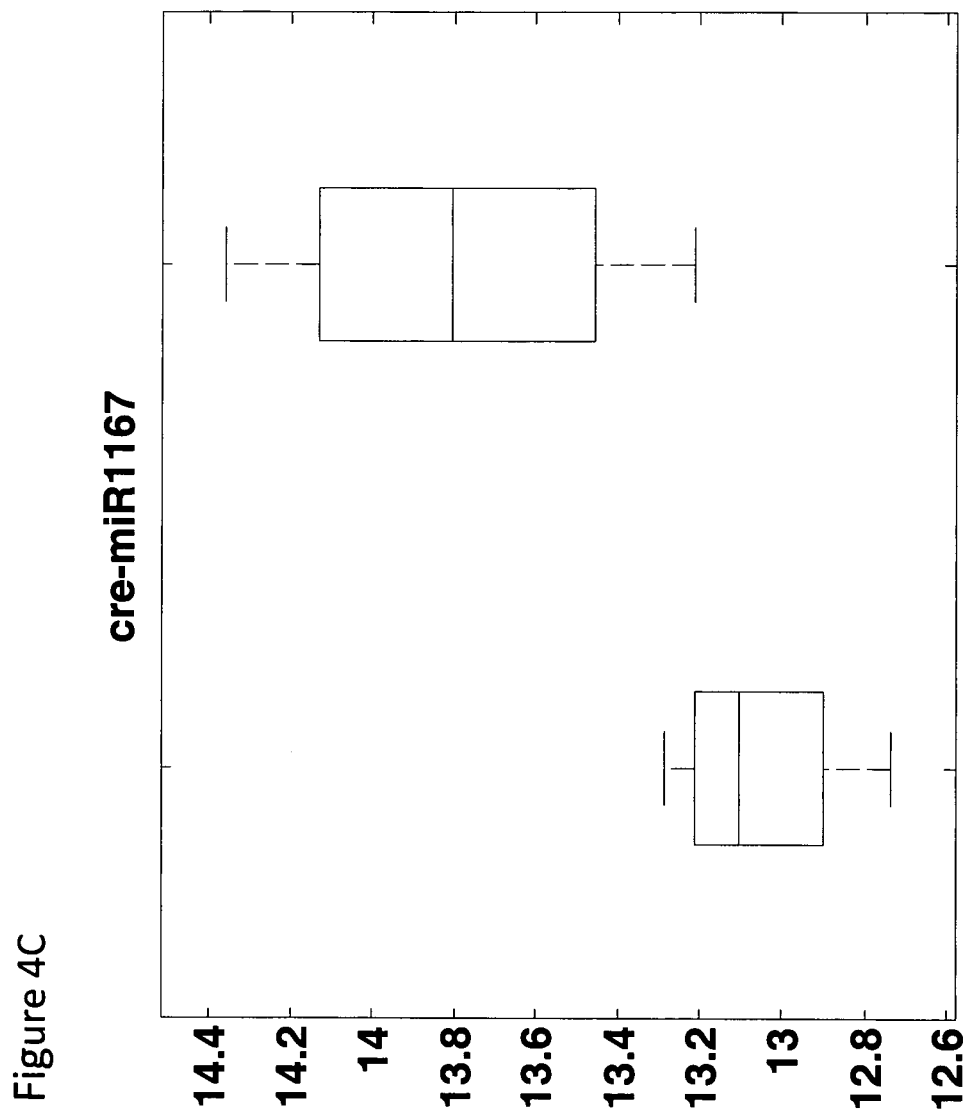
Figure 4D:
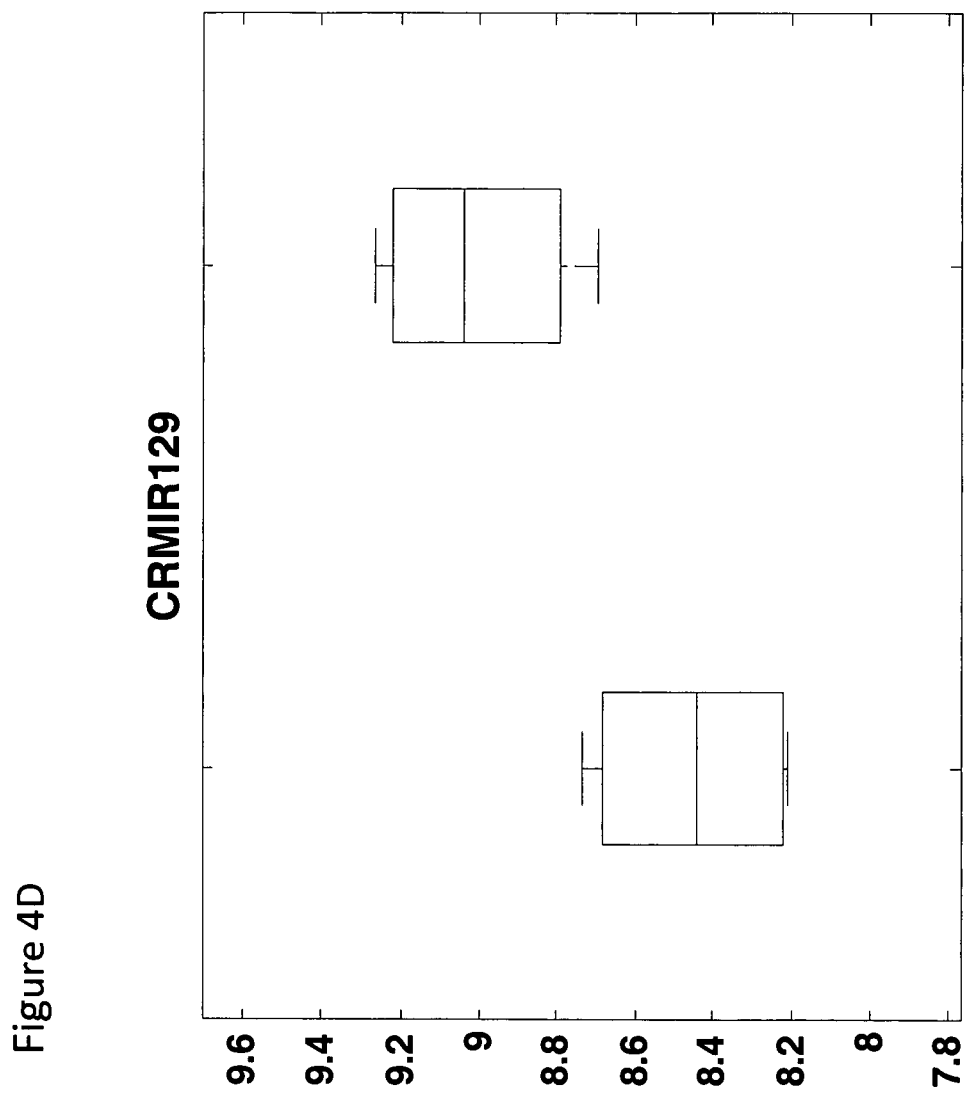
Figure 4E:
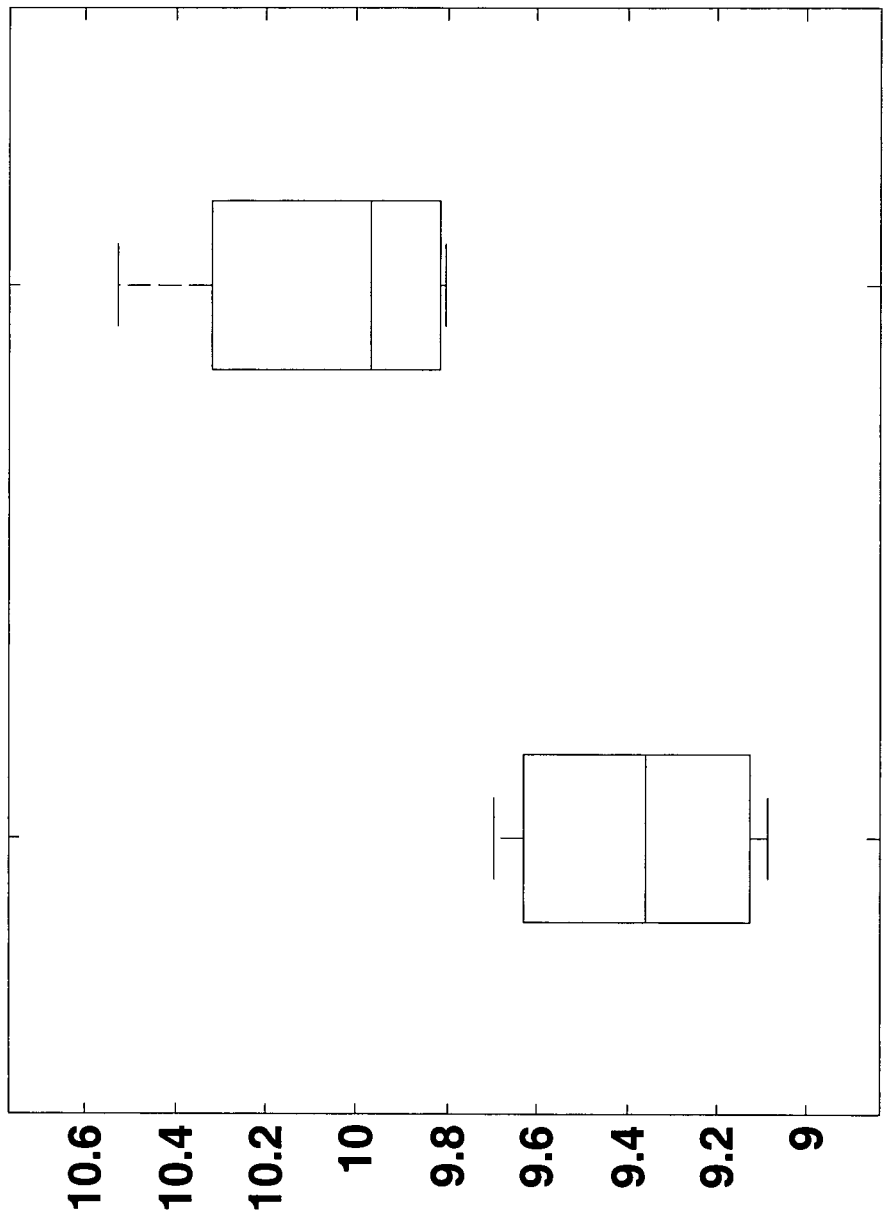

The differential expression of microRNAs in nitrate-limiting relative to nitrate-sufficient conditions is further exemplified in the scatterplot of FIG. 3, and in the boxplots of FIGS. 4A-4E.

Expression of CRMIR136 (SEQ ID NO: 72) was validated by qRT-PCR as follows: Briefly, RNA was incubated in the presence of a poly A polymerase enzyme (Takara, Otsu Japan), $MnCl_2$, and ATP for 1 h at 37° C. Then, using an oligo dT primer harboring a consensus sequence, reverse transcription was performed on total RNA using SuperScript II RT (Invitrogen, Carlsbad Calif.). Next, the cDNA was amplified by real time PCR; this reaction contained a microRNA-specific forward primer and a universal reverse primer complementary to the consensus 3' sequence of the oligo dT tail. Results represent the median of four repeats with each one done in triplicate and the signal was normalized against the median of three reference microRNAs. The sequences used in the PCR procedure are detailed in table 5 below:

TABLE 5

Sequences used in PCR validation of CRMIR136 (SEQ ID NO: 72) expression

| Role in PCR | Sequence | SEQ ID NO: |
|---|---|---|
| oligo dT primer | GCGAGCACAGAATTAATACGACT CACTATCGGTTTTTTTTTTTTVN[1] | 79 |
| microRNA-specific forward primer | TGCGGGATCCAGTGCTGG | 76 |
| universal reverse primer | GCGAGCACAGAATTAATACGAC | 77 |

[1]V represents A, G or C, and N represents any nucleotide.

Accordingly, the differential expression of CRMIR136 (SEQ ID NO: 72) was validated by qRT-PCR, as it was found to be downregulated in nitrate-limiting relative to nitrate-sufficient conditions with a fold-change of 1.5 (p value=0.01), which correlates with the fold change of 1.5 identified by the microarray experiments.

Example 4

Oil Content in Transformed *C. Reinhardtii* Cells

Synthetic DNA clones were synthesized by Genscript. These clones contained, respectively, the hairpins cre-mir1151b (SEQ ID NO: 48), cre-mir1157 (SEQ ID NO: 51), CRMIR121 (SEQ ID NO: 66). An additional clone contained a sequence consisting of the mature microRNA sequence of CRMIR5 inserted in the backbone of cre-mir1162 as follows: CATATGGCGGGGCCCTGACACCACTGCG-GCCGTAGGACGGCTAGATCCGGGACC GCGCCTG-GACCCGAGGGAGGACCCCTCGGGACCCG-GTACGTCGTCCCGGATCTA GC, hereby designated SEQ ID NO: 78. (This artificial sequence, bearing the mature microRNA sequence of CRMIR5, was created because the endogenous hairpin of CRMIR5 (SEQ ID NO: 57) comprises sequences of various mature microRNAs, and therefore is less suitable for transformation.)

The vectors were designed to contain an NdeI site at their 5' end and an EcoRI site at their 3' end and were constructed in the pUC19 vector. The vectors were digested with NdeI and EcoRI to release the fragments containing the indicated microRNAs, which was cloned to the pGenD-Ble vector (N. Fischer & J. D. Rochaix, Molecular General Genomics, 2001, 265:888-894). pGenD-Ble was previously digested with NdeI and EcoRI to release the ble gene. The digested pGenD-Ble vector was separated by gel electrophoresis and the fragment containing the vector minus the ble gene was ekcised from the gel.

The resulting vector containing the pGenD promoter-microRNA hairpin-and pGenD terminator were designated pGenD-1151, pGenD-1157, pGenD-CR121 and pGenD-CR5in1162. The vectors were co-transformed into *C. Reinhardtii* cw15 together with pGenD-Aph following the method described by K Kindle (K. L. Kindle, Proc. Natl. Acad. Sci. U.S.A. 93 (1990) 13689-13693). PgenD-Aph was prepared by introducing the Aph gene (I. Sizova, M. Fuhrmann and P. Hegemann, Gene 277 (2001) 221-229) between the NdeI and EcoRI sites of pGenD-Ble as described above. Cells were selected on TAP medium containing 15 microgram/ml paromomycin.

Cell cultures were grown in Bristol medium, and relative evaluation of neutral lipids content was performed as described in example 3.1 above.

Table 6 below provides results of oil content evaluation in four transformed *C. Reinhardtii* lines (several clones for each line) overexpressing different microRNAs. For each line, unless stated otherwise, two experiments were performed in 50 ml tubes containing 10 ml of TAP growth medium and a third experiment was performed in 250 ml flasks containing 50 ml of TAP.

Oil content in transformed lines of *C. Reinhardtii* is depicted in FIGS. 2A-2D.

TABLE 6

Oil content in transformed *C. Reinhardtii* lines overexpressing microRNA, relative to oil content in controls.

| Overexpressed microRNA | line | Clone | 10 ml medium Exp 1 | 10 ml medium Exp 2 | 50 ml medium |
|---|---|---|---|---|---|
| CR5 in cre-miR1162 | 5 | 4 | 1.34 ± 0.05 | 1.34 ± 0.2 | 1.20 ± 0.04 |
| | | 7 | 1.36 ± 0.16 | 1.18 ± 0.05 | 1.25 ± 0.11 |
| | | 9 | 1.71 ± 0.30 | 0.95 ± 0.09 | 1.17 ± 0.03 |
| | | 11 | 1.60 ± 0.17 | 1.18 ± 0.05 | 1.27 ± 0.12 |
| | | 12 | 1.49 ± 0.27 | 0.96 ± 0.07 | 1.18 ± 0.12 |
| | | 18 | 1.28 ± 0.16 | 0.94 ± 0.1 | 1.22 ± 0.05 |
| | | 20 | 1.39 ± 0.18 | 1.03 ± 0.1 | 1.26 ± 0.01 |
| | | 28 | 1.45 ± 0.15 | 1.16 ± 0.11 | 1.55 ± 0.11 |
| miR-1151b | 1151 | 13 | 1.49 ± 0.09 | 0.97 ± 0.04 | 1.09 ± 0.02 |
| | | 19 | 1.45 ± 0.11 | 0.97 ± 0.07 | 1.31 ± 0.02 |
| | | 24 | 1.95 ± 0.84 | 1.09 ± 0.07 | 1.00 ± 0.04 |
| | | 25 | 1.58 ± 0.1 | 1.13 ± 0.28 | 1.76 ± 0.01 |
| | | 30 | 1.76 ± 0.07 | 1.09 ± 0.11 | 1.04 ± 0.07 |
| miR-1157 | 1157 | 3 | 2.24 ± 0.84 | 0.97 ± 0.03 | 1.08 ± 0.03 |
| | | 12 | 1.92 ± 0.41 | 1.01 ± 0.13 | 1.17 ± 0.01 |
| | | 13 | 1.74 ± 0.17 | 1.01 ± 0.13 | 1.00 ± 0.05 |
| | | 14 | 1.88 ± 0.21 | 1.04 ± 0.02 | 1.12 ± 0.05 |
| | | 16 | 2.87 ± 0.64 | 0.99 ± 0.06 | 1.14 ± 0.1 |
| | | 22 | 1.59 ± 0.09 | 1.18 ± 0.06 | 1.07 ± 0.03 |
| | | 24 | 2.21 ± 0.86 | 0.96 ± 0.02 | 1.24 ± 0.04 |
| miR-121 | 121 | 9 | NA[1] | 1.15 ± 0.33 | 1.17 ± 0.09 |
| | | 16 | NA | 1.25 ± 0.05 | 1.41 ± 0.07 |
| | | 19 | NA | 1.06 ± 0.17 | 1.24 ± 0.05 |
| | | 20 | NA | 1.08 ± 0.08 | 1.13 ± 0.06 |
| | | 30 | NA | 1.11 ± 0.08 | 1.23 ± 0.08 |

[1]Not applicable

Example 5

MicroRNA Targets

A differentially expressed microRNA identified, is cre-miR1167 (SEQ ID NO: 21), that was downregulated under nitrate-limiting conditions. cre-miR1167 (SEQ ID NO: 21) is predicted to target a CYP51 homologue, which encodes a cytochrome p450 sterol-14α-demethylase: a conserved key enzyme in sterol biosynthesis {Lepesheva, 2007 *Biochim Biophys Acta.* 2007 March; 1770(3): 467-477}. We are not aware of any work done in characterizing CYP51 in algae but cyp51 mutants are considered to be lethal in other unicellular organisms. Interestingly, a screen for small molecule activators of the integrated stress response (ISR) identified two related compounds that also activated sterol-regulated genes by blocking cholesterol biosynthesis {Harding, 2005 *Cell Metab.* 2005 December; 2(6): 361-371}. The ISR is known to adapt cells to ER stress, a phenomenon that is modulated by a KDEL receptor like a putative target of CRMIR136 (SEQ ID NO: 72).

Phosphoglycerate mutase is the target gene of CRMIR152 (SEQ ID NO: 38), which was found to be significantly downregulated under both nitrogen starvation and strong light (Tables 2b and 3b respectively). This enzyme is involved in glycolysis, which is the process in which glucose is converted to pyruvate, which can be further converted to acetyl coenzyme A (acetyl CoA). Acetyl CoA is the main substrate for fatty acid biosynthesis. Accordingly, embodiments of the invention include generation of transgenic algal strains which overexpress phosphoglycerate mutase modified such that the binding of CRMIR152 (SEQ ID NO: 38) is eliminated.

Additionally, the enzyme fructose 1,6 bisphosphatase is the target of CRMIR5 (SEQ ID NO: 26) which was found to be upregulated under strong light treatment (Table 3a). This enzyme participates in gluconeogenesis, which is the process in which glucose is re-formed from pyruvate and is therefore the opposite process of glycolysis. Accordingly, embodiments of the invention further include generating transgenic algal strains which overexpress CRMIR5 (SEQ ID NO: 26).

It is possible that CRMIR152 (SEQ ID NO: 38) and CRMIR5 (SEQ ID NO: 26) work together to increase the pool of free acetyl CoA when increased oil biosynthesis is required by upregulating glycolysis and down regulating gluconegenesis. Accordingly, the invention further relates to transgenic algal strains which overexpress both modified phosphoglycerate mutase and CRMIR5.

Another pair of microRNAs possibly working in co-regulation of their targets is CRMIR123 (SEQ ID NO: 36) and CRMIR121 (SEQ ID NO: 35), which is upregulated in strong light. They are both located on two tandem hairpins in the same locus. CRMIR121 (SEQ ID NO: 35) is predicted to target a gene encoding histone deacetylase (HDAC) and CRMIR123 (SEQ ID NO: 36) is predicted to target a gene encode histone acetyltransferase (HAT), two enzymes that function as general suppressors or activators of transcription accordingly. The two microRNAs being physically linked suggests they might be under the same regulation and function together to keep appropriate balance between HDAC and HAT.

Target prediction can allow manipulation of microRNA regulation by expressing a microRNA-resistant target; a gene where silent mutations were introduced in the microRNA-binding site thus bypassing the microRNA regulation. Alternatively, manipulation of microRNA regulation can be performed by microRNA overexpression. Both these strategies have been used in plants and have resulted in significant phenotypes alterations.

The Web MicroRNA Designer2 (WMD2) tool {Stephan Ossowski, Rebecca Schwab, Detlef Weigel (2008), The Plant Journal 53 (4), 674-690} was used to predict the targets of selected microRNAs that were found to be differentially expressed relative to changes in lipid content. The default settings of the WMD2 were used to perform the search: up to 5 mismatches, hybridization temperature of 23° C. and minimum hybridization energy efficiency of 70% from that of the perfect match (dG).

Some of the genes predicted to be targeted by the differentially-expressed microRNAs are known to be stress-regulated or to be involved in stress responses. This includes some of the genes predicted to be targeted by CRMIR136 (SEQ ID NO: 72) such as the Jumonji-encoding gene JMJC, which was found to be draught-induced in *Nicotiana benthamiana* and Virus-Induced Gene Silencing (VIGS) of the JMJC gene in *N. benthamiana* caused relative drought tolerant phenotypes. Another stress-regulated predicted target of CRMIR136 is a KDEL receptor, a protein known to modulate the endoplasmic reticulum (ER) stress response in human cell culture {Yamamoto, 2003 THE JOURNAL OF BIOLOGICAL CHEMISTRY Vol. 278, No. 36, pp. 34525-34532, 2003}. The ER stress response is initiated by an increase in misfolded proteins in the ER and includes an induction of the synthesis of ER chaperones, suppression of general protein synthesis and enhancement of the ER-associated degradation of misfolded proteins.

5.1 Differential Expression of ADCY33 (SEQ ID NO: 80), a Predicted Target of CRMIR136 (SEQ ID NO: 72) in Nitrate-Limiting and Nitrate Sufficient Conditions The adenylate cyclase-encoding gene ADCY33 (SEQ ID NO: 80) is another predicted target of CRMIR136 (SEQ ID NO: 72) and its expression, in nitrate-limiting and nitrate sufficient conditions, was assessed by qRT-PCR according as follows:

I. cDNa was prepared from the RNA extracted as described in example 3, by the steps of the following protocol:
1. 1 µg total RNA in 4 µl DDW.
2. Incubate at 85° C. for 2 min and put on ice.
3. Add on ice reaction mixture 6 µl:

| Component | volume (µl) |
|---|---|
| 5X buffer | 2 |
| 0.1M DTT | 1 |
| RNAsin | 0.5 |
| Oligo dT primer (10 µM stock) | 1 |
| 10 mM dNTP's | 0.5 |
| RT superscript II | 0.5 |
| DDW | 0.5 |

4. 1 h at 42° c.
5. 85° C. for 2 min
6. Spin and place on ice.
Final concentration: 100 ng/µl, total of 10 µl.
Make dilution of 10 ng/µl
PCR program 85 42 RT in machine no. 238
The sequences used in the PCR procedure are detailed in table 7 below:

TABLE 7

Sequences used in qRT-PCR assay of ADCY33 (SEQ ID NO: 80) expression

| Role in PCR | Sequence | SEQ ID NO: |
|---|---|---|
| Oligo dT primer | TTTTTTTTTTTTTTTTTTV | 81 |
| Forward primer | ATGATGGGCCTCATGGTCTA | 82 |
| Reverse primer | CCAGGATGTCGTTGATGATG | 83 |

II. Real time PCR using SYBR mRNA was preformed by the steps of the following protocol:
1. Divide the Fwd primers into 96-well plate and spin it down.
2. Take out the cDNA, defrost and keep on ice.
   Dilute the cDNA: 100 ng/µl→10 ng/µl
   Replace tip between adding cDNA and mixing it in the DDW!
3. In the PCR room assemble (at room temp.) in 2 ml tube:

| Component | volume |
|---|---|
| SYBR Green | 10 µl |
| DDW | 7 µl |

4. Flip the tube, vortex and short spin. Put the mix on ice.
5. Add (outside of the PCR room, using Gilson 200):

| Component | volume |
|---|---|
| cDNA 0.05 ng/µl | 1 µl |
| Total Vol | 18 µl |

Mix by flipping, vortex and short spin.
6. Divide 18 µl from the mix into each well, using the stepper from the PCR room.
7. Add 1 µl Fwd primer 1 µl Rev primer.
Use the PCR-multi-channel.

8. Short spin the plate and start the reaction.
9. The reaction program:
stage 1, Reps=1
step 1: Hold @ 95.0 C for 10:00 (MM:SS), Ramp Rate=100
Stage 2, Reps=40
Step 1: Hold @ 95.0 C for 0:15 (MM:SS), Ramp Rate=100
Step 2: Hold @ 60.0 C for 1:00 (MM:SS), Ramp Rate=100
Dissociation Protocol:
Stage 3, Reps=1
Step 1: Hold @ 95.0 C for 0:15 (MM:SS), Ramp Rate=Auto
Step 2: Hold @ 60.0 C for 1:00 (MM:SS), Ramp Rate=Auto
Step 3: Hold @ 95.0 C for 0:15 (MM:SS), Ramp Rate=Auto
Standard 7500 Mode
Sample Volume (µL): 20.0
Data Collection: Stage 2, Step 2

Figure 5:
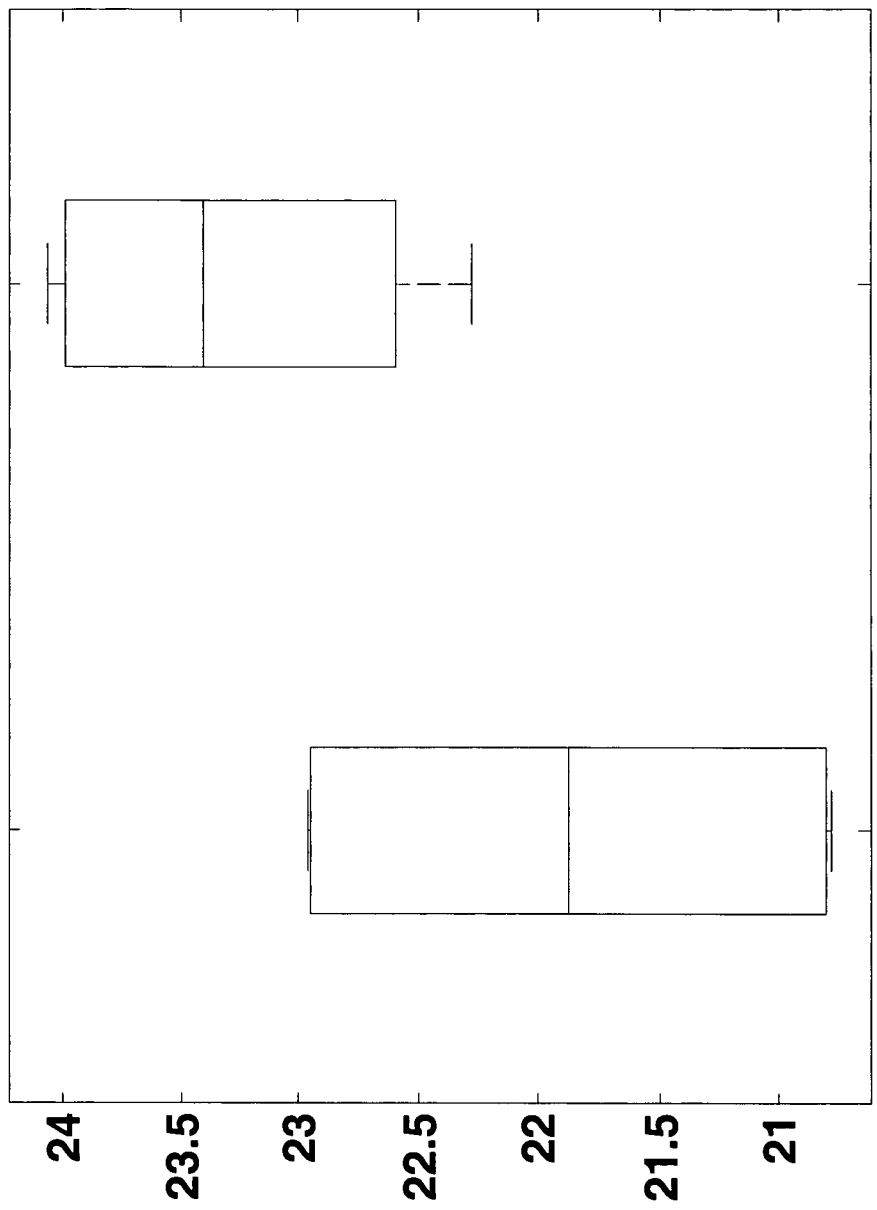
FIG. 5 is a boxplot presentation comparing distributions of the expression values (Y axis) of the adenylate cyclase-encoding gene ADCY33 (SEQ ID NO: 80) in nitrate-limiting conditions (the right box) vs. nitrate-sufficient conditions (the left box). The line in the box indicates the median expression value, the box top and bottom boundaries indicate the 75th and 25th percentiles respectively, and the horizontal lines and crosses (outliers) show the full range of signals in each group.

As indicated in FIG. 5, the expression of ADCY33 (SEQ ID NO: 80) was found by qRT-PCR to be 2.9-fold induced under nitrate-limiting conditions.

Nitrogen starvation is required for inducing sexual differentiation in *C. reinhardtii* {Goodenough, 2007, Sex determination in Chlamydomonas. Semin Cell Dev Biol 2007, 18(3): 350-361}. One of the first events following sexual differentiation induction is a protein kinase-dependent activation of a flagellar adenylate cyclase that causes a 10 fold increase in cAMP concentrations {Zhang et al., 1996; Cell adhesion-dependent inactivation of a soluble protein kinase during fertilization in Chlamydomonas. Mol Biol Cell 1996, 7(4):515-527}. The finding that the expression of ADCY33 (SEQ ID NO: 80) is upregulated under nitrate-limiting conditions correlates with the need of increased cAMP levels during *C. reinhardtii* sexual differentiation.

5.2 Introduction of microRNA Resistant Target Genes

Synthetic DNA clones containing the cDNA sequences of the miR-resistant targets according to table 8 below were synthesized by Genscript.

TABLE 8

Sequences of microRNA resistant target genes

| miR | microRNA resistant target gene SEQ ID NO |
|---|---|
| CRMIR152 (SEQ ID NO: 38) | 86 |
| CR167 (SEQ ID NO: 84) | 87 |
| cre-miR1167 (SEQ ID NO: 21) | 88 |

The clones were designed to contain an NdeI site at their 5' end and an EcoRI site at their 3' end and were constructed in the pUC19 vector. The vectors were digested with NdeI and EcoRI to release the fragments containing the indicated sequences, which were cloned to the pGenD-Ble vector (N. Fischer & J. D. Rochaix, Molecular General Genomics, 2001, 265:888-894). pGenD-Ble was previously digested with NdeI and EcoRI to release the ble gene. The digested pGenD-Ble vector was separated by gel electrophoresis and the fragment containing the vector minus the ble gene was excited from the gel.

The resulting vector containing the pGenD promoter-miR-resistant target-and pGenD terminator were designated pGenD-CR152R, pGenD-167R and pGenD-1167R. The vectors were co-transformed into *Chlamydomonas Reinhardtii* cw15 together with pGenD-Aph following the method described by K Kindle (K. L. Kindle, Proc. Natl. Acad. Sci. U.S.A. 93 (1990) 13689-13693). PgenD-Aph was prepared by introducing the Aph gene (I. Sizova, M. Fuhrmann and P. Hegemann, Gene 277 (2001) 221-229) between the NdeI and EcoRI sites of pGenD-Ble as described above. Cells were selected on TAP medium containing 15 microgram/ml paromomycin.

The foregoing description of the specific embodiments so fully reveals the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It should be understood that the detailed description and specific examples, while indicating preferred embodiments of the invention, are given by way of illustration only, since various changes and modifications within the spirit and scope of the invention will become apparent to those skilled in the art from this detailed description.

The invention claimed is:

1. A transgenic algae transformed with an expression construct comprising a heterologous promoter operably linked to a nucleic acid molecule selected from the group consisting of SEQ ID NO: 13, 14, 47 or 48, or a nucleic acid molecule having at least 95% identity to said nucleic acid molecule.

2. The transgenic algae of claim 1, wherein the promoter is selected from the group consisting of a constitutive promoter and an inducible promoter.

3. The transgenic algae of claim 1, wherein said algae is selected from the group consisting of *Neochloris oleoabundans, Scenedesmus dimorphus, Euglena gracilis, Phaeodactylum tricornutum, Pleurochlysis carterae, Tetraselmis chui, Tetraselmis suecica, Isochrysis galbana, Nannochloropsis salina, Nannochloropsis oculata, Botryococcus braunii, Dunaliella tertiolecta, Nannochloris* sp., *Spirulina* sp., *Chlorella* sp., *Oypthecodinium cohnii, Cylindrotheca* sp., *Dunaliella primolecta, Monallanthus salina, Nitzschia* sp., *Schizochytrium* sp. and *Tetraselmis sueica*.

4. The transgenic algae of claim 1, wherein said algae is selected from the group consisting of *Chlamydomonas reinhardtii, Chlorella vulgaris* and *Phaeodactylum tricornutum*.

5. A method for altering the oil content in *C reinhardtii* algae, comprising introducing into the *C. reinhardtii* algae a construct comprising a heterologous promoter operably linked to a nucleic acid molecule selected from the group consisting of SEQ ID NO: 13, 14, 47 or 48, or a nucleic acid molecule having at least 95% identity to said nucleic acid molecule, and wherein the oil content of the *C. reinhardtii* algae is altered.

6. The transgenic algae of claim 1, wherein said nucleic acid has at least 98% identity to SEQ ID NO. 13, 14, 47 or 48.

7. The transgenic algae of claim 1, wherein the transgenic algae belongs to phyla *Chlorophyta*.

8. The transgenic algae of claim 1, wherein the transgenic algae is *C. reinhardtii* and wherein the transgenic algae has increased oil content relative to a non-transgenic control algae.

9. The method according to claim 5, wherein said nucleic acid has at least 98% identity to SEQ ID NO. 13, 14, 47 or 48.

10. The method according to claim 5, further comprising growing said *C. reinhardtii* algae following introducing said construct and identifying algae having altered oil content.

* * * * *